(12) United States Patent
Sakaida

(10) Patent No.: US 6,421,419 B1
(45) Date of Patent: Jul. 16, 2002

(54) ENERGY SUBTRACTION PROCESSING METHOD AND APPARATUS

(75) Inventor: Hideyuki Sakaida, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/986,388

(22) Filed: Nov. 8, 2001

(30) Foreign Application Priority Data

Nov. 8, 2000 (JP) ........................................ 2000-339855
Nov. 8, 2000 (JP) ........................................ 2000-339859

(51) Int. Cl.$^7$ ................................................ H05G 1/64
(52) U.S. Cl. ................. 378/98.11; 378/98.9; 378/98.12
(58) Field of Search ........................ 378/98.11, 98.12, 378/98.9, 5

(56) References Cited

U.S. PATENT DOCUMENTS

| | | | |
|---|---|---|---|
| 4,813,061 A | * | 3/1989 | Kakegawa ................. 250/583 |
| 4,855,598 A | | 8/1989 | Ohgoda et al. |
| 4,896,037 A | | 1/1990 | Shimura et al. |
| 5,485,371 A | | 1/1996 | Ito et al. |
| 6,016,356 A | * | 1/2000 | Ito et al. ...................... 382/132 |
| 6,326,636 B1 | * | 12/2001 | Isoda et al. ................. 250/584 |

* cited by examiner

Primary Examiner—David V. Bruce
Assistant Examiner—Pamela R. Hobden
(74) Attorney, Agent, or Firm—Sughrue Mion, PLLC

(57) ABSTRACT

Each of image signals representing radiation images of a single object is weighted with a weight factor. Signal components of the weighted image signals representing corresponding pixels in the radiation images are subtracted from each other, and a difference signal representing an image of a specific structure of the object is obtained. The weight factor is set for each pixel in each radiation image and in accordance with a difference between logarithmic values of radiation doses with respect to corresponding pixels in the radiation images, or in accordance with a logarithmic value of a ratio between the radiation doses with respect to the corresponding pixels in the radiation images.

27 Claims, 15 Drawing Sheets

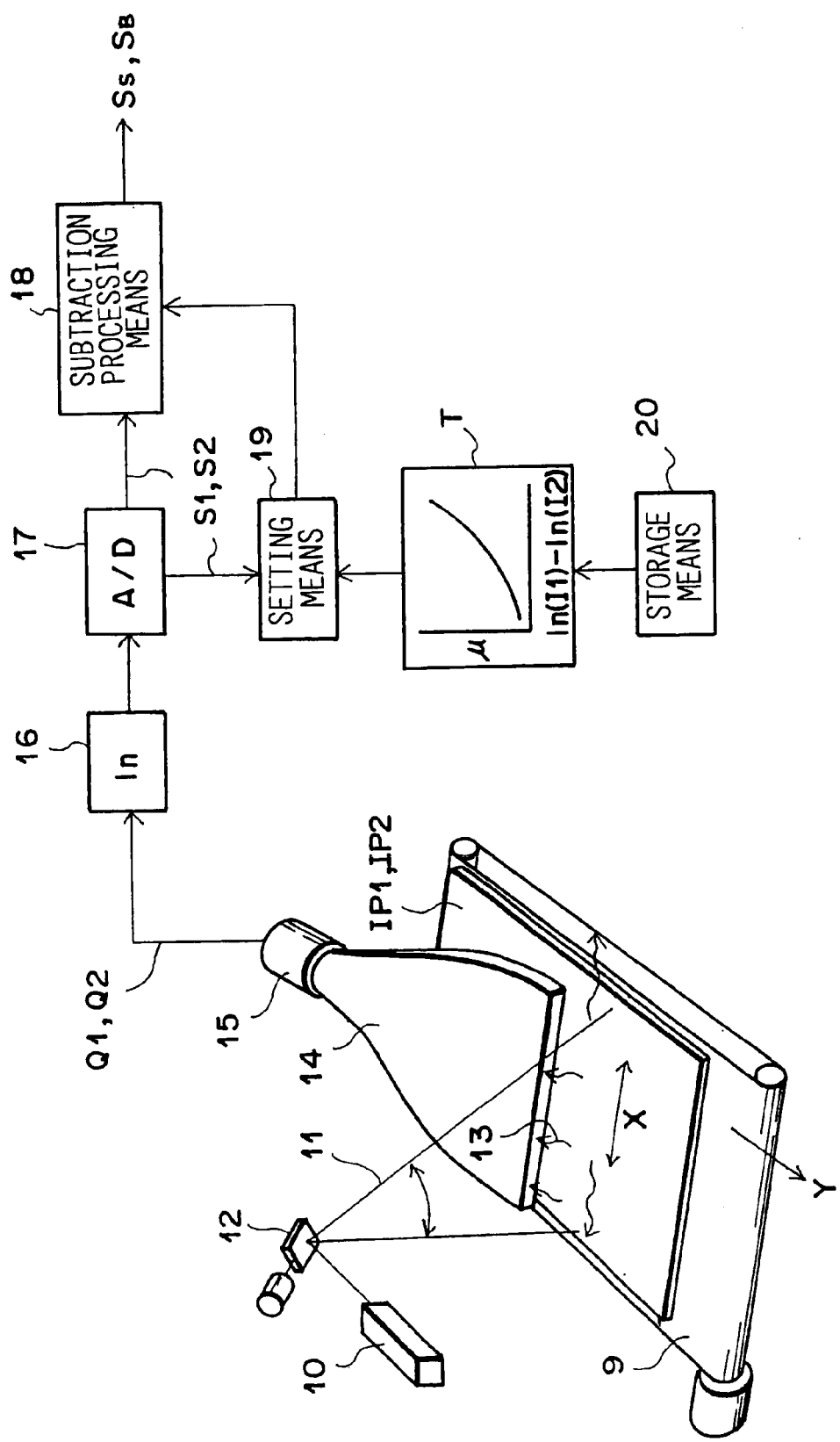

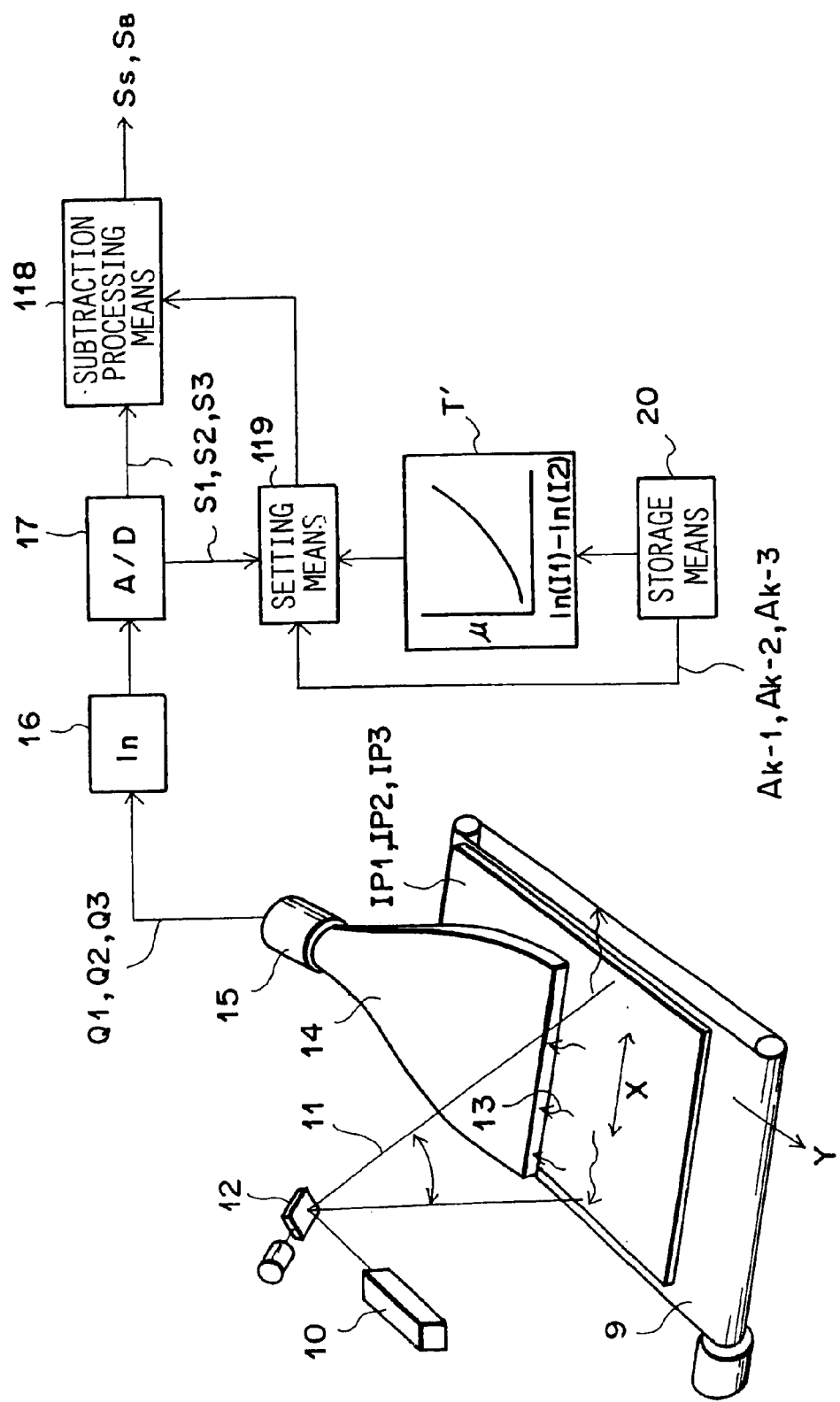

FIG. 9

19A — MEAN ATTENUATION COEFFICIENT CALCULATING MEANS

| LOGARITHMIC RADIATION DOSE DIFFERENCE | TABLE | MEAN ATTENUATION COEFFICIENT |
|---|---|---|
| $\ln(I1) - \ln(I2) \rightarrow$ | | $\rightarrow \mu_1(IP1), \mu_1(IP2), \mu_1(IP3)$ |
| $\ln(I1) - \ln(I3) \rightarrow$ | | $\rightarrow \mu_2(IP1), \mu_2(IP2), \mu_2(IP3)$ |
| $\ln(I2) - \ln(I3) \rightarrow$ | | $\rightarrow \mu_3(IP1), \mu_3(IP2), \mu_3(IP3)$ |

19B — WEIGHTED MEAN VALUE CALCULATING MEANS ← $Ak_{-1}, Ak_{-2}, Ak_{-3}$ $\mu_T(IP1)(\overline{\mu_B}, \overline{\mu_S})$
$\mu_T(IP2)(\overline{\mu_B}', \overline{\mu_S}')$
$\mu_T(IP3)(\overline{\mu_B}'', \overline{\mu_S}'')$

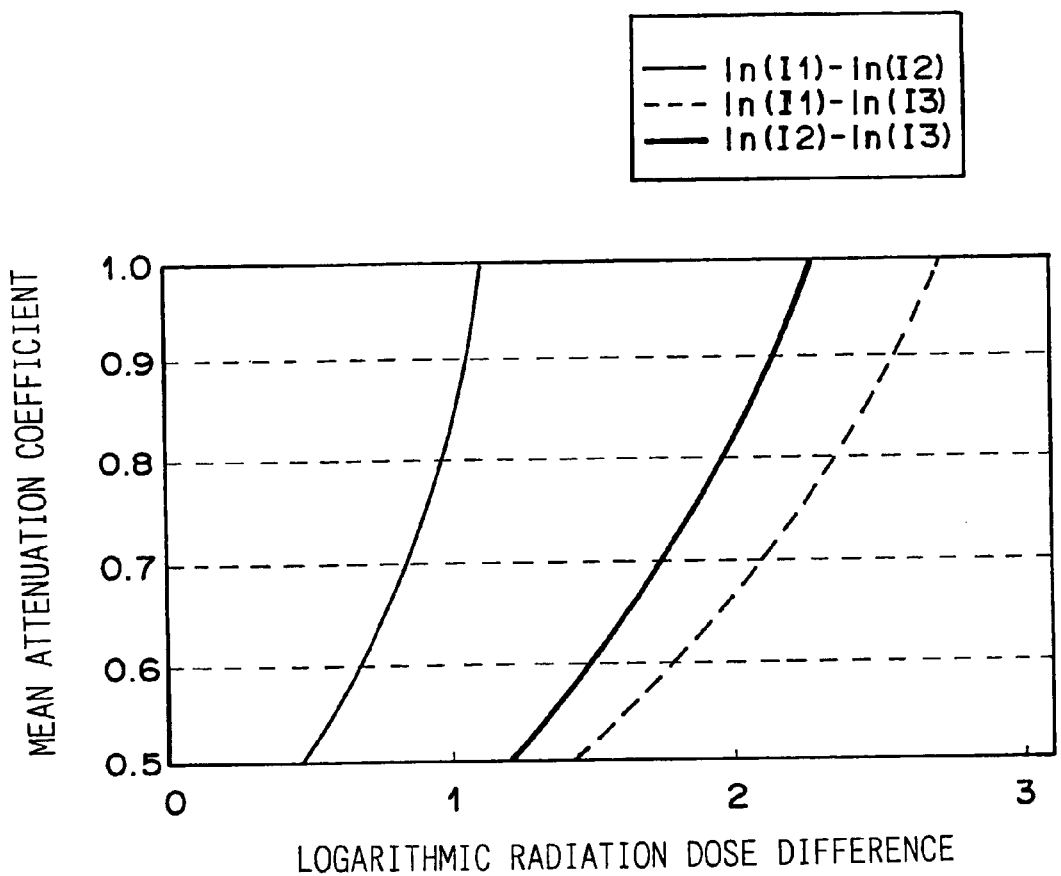

ENERGY SUBTRACTION PROCESSING METHOD AND APPARATUS

BACKGROUND OF THE INVENTION

1. Field of the Invention

This invention relates to an energy subtraction processing method and apparatus, wherein energy subtraction processing is performed on a plurality of image signals representing radiation images of an object. This invention also relates to a recording medium, on which a program for causing a computer to execute the energy subtraction processing method has been recorded and from which the computer is capable of reading the program.

2. Description of the Related Art

It has been proposed to use stimulable phosphors in radiation image recording and reproducing systems. Specifically, a radiation image of an object, such as a human body, is recorded on a sheet provided with a layer of the stimulable phosphor (hereinafter referred to as a stimulable phosphor sheet). The stimulable phosphor sheet, on which the radiation image has been stored, is then exposed to stimulating rays, such as a laser beam, which cause the stimulable phosphor sheet to emit light in proportion to the amount of energy stored thereon during its exposure to the radiation. The light emitted by the stimulable phosphor sheet, upon stimulation thereof, is photoelectrically detected and converted into a digital image signal. The image signal is then processed and used for the reproduction of the radiation image of the object as a visible image on a recording material.

Also, techniques for performing energy subtraction processing on radiation images have heretofore been known. (The energy subtraction processing techniques are disclosed in, for example, U.S. Pat. Nos. 4,855,598 and 4,896,037, 5,485,371.) With the energy subtraction processing techniques, an object is exposed to several kinds of radiation having different energy distributions. Alternatively, the energy distribution of the radiation carrying image information of an object is changed after the radiation has been irradiated onto one of a plurality of radiation detecting means (e.g., the stimulable phosphor sheets described above), after which the radiation impinges upon the second radiation detecting means. In this manner, a plurality of radiation images, in which different images of a specific structure of the object are embedded, are obtained. Thereafter, image signal components of the image signals representing the plurality of the radiation images, which image signal components represent corresponding pixels in the radiation images, are multiplied by appropriate weight factors, and the thus weighted image signal components are subjected to a subtraction process. From the subtraction process, a difference signal, which represents only the image of the specific structure of the object, is obtained. By the utilization of the thus obtained difference signal, a visible radiation image, which represents only the specific structure of the object, is capable of being reproduced.

In the aforesaid radiation image recording and reproducing systems utilizing the stimulable phosphor sheets, the radiation image having been stored on the stimulable phosphor sheet is read out directly as an electric image signal. Therefore, with the radiation image recording and reproducing systems, the energy subtraction processing is capable of being performed easily. In cases where the energy subtraction processing is to be carried out by using the stimulable phosphor sheets, radiation images may be stored on, for example, two stimulable phosphor sheets such that the parts of the radiation images corresponding to a specific structure may be different in the two radiation images. For such purposes, a two-shot energy subtraction processing technique may be employed wherein the operation for recording a radiation image is performed twice with two kinds of radiation having different energy distributions. Alternatively, a one-shot energy subtraction processing technique may be employed wherein, for example, two stimulable phosphor sheets placed one upon the other (they may be in contact with each other or spaced away from each other) are simultaneously exposed to radiation, which carries image information of an object, such that the two stimulable phosphor sheets are exposed to radiation having different energy distributions. In cases where the two-shot energy subtraction processing technique is employed, and radiation images are to be recorded on an increased number of the stimulable phosphor sheets, the same number of image recording operations as that of the stimulable phosphor sheets are performed. For example, in cases where the two-shot energy subtraction processing technique is employed, and radiation images are to be recorded on three stimulable phosphor sheets, three image recording operations are performed. Therefore, in this specification, the energy subtraction processing technique, in which multiple image recording operations are performed, is referred to as the multi-shot energy subtraction processing technique (including the two-shot energy subtraction processing technique).

With the energy subtraction processing techniques utilizing the stimulable phosphor sheets, for example, in cases where the object is a human body, two radiation images of the human body may be formed on the stimulable phosphor sheets with two kinds of radiation having different energy distributions (i.e., radiation having a high energy level and radiation having a low energy level), and two image signals representing the two radiation images may be obtained. Also, the two image signals may be weighted with appropriate weight factors, and the difference signal may be obtained by performing a subtraction process on the weighted image signals. In this manner, a radiation image, in which only the pattern of a soft tissue of the human body is illustrated, and a radiation image, in which only the pattern of a bone of the human body is illustrated, are capable of being obtained. The operation processing is performed in the manner described below. Specifically, the first stimulable phosphor sheet, upon which the radiation having a low energy level impinges, may be represented by IP1, and the second stimulable phosphor sheet, upon which the radiation having a high energy level impinges, may be represented by IP2. Also, a logarithmic value of a radiation dose (i.e., a logarithmic radiation dose), which the first stimulable phosphor sheet IP1 receives, may be represented by L, and the logarithmic value of the radiation dose (i.e., the logarithmic radiation dose), which the second stimulable phosphor sheet IP2 receives, may be represented by H. In such cases, L and H may be represented respectively by Formula (1) and Formula (2) shown below.

$$L = -\overline{\mu_S} t_S - \overline{\mu_B} t_B + L_0 \qquad (1)$$

$$H = -\overline{\mu_S}' t_S - \overline{\mu_B}' t_B + H_0 \qquad (2)$$

wherein
$\overline{\mu_B}$ represents the mean attenuation coefficient of the bone with respect to the first stimulable phosphor sheet IP1,
$\overline{\mu_S}$ represents the mean attenuation coefficient of the soft tissue with respect to the first stimulable phosphor sheet IP1, $\overline{\mu_B}'$ represents the mean attenuation coefficient of the bone with respect to the second stimulable phosphor sheet IP2, $\overline{\mu_S}'$ represents the mean attenuation coefficient of the soft tissue with respect to the second stimulable phosphor sheet IP2, $t_S$ represents the thickness of the bone, $t_B$ represents the thickness of the soft tissue, and each of $L_0$ and $H_0$ represents the fixed number depending upon the radiation source.

As the logarithmic radiation doses L and H, the image signals having been obtained from the stimulable phosphor sheets IP1 and IP2 may be employed respectively.

A substance has a radiation attenuation coefficient depending upon radiation energy. Also, in cases where the radiation irradiated to the object is not monochromatic and is distributed over a certain energy range, the energy distribution of the detected radiation (e.g., the radiation impinging upon the stimulable phosphor sheet) changes depending upon the thickness of a substance contained in the object (in cases where the object is the human body, a bone or a soft tissue). Such a phenomenon is referred to as the beam hardening. Therefore, the radiation attenuation coefficient of the substance is weighted with the energy distribution of the detected radiation and averaged. The thus obtained value is defined as the mean attenuation coefficient. Accordingly, the mean attenuation coefficient varies for different thicknesses of the substance.

In cases where L represented by Formula (1) shown above is multiplied by the factor of $\overline{\mu_B}'$, and H represented by Formula (2) shown above is multiplied by the factor of $\overline{\mu_B}$, the difference between $\overline{\mu_B}H$ and $\overline{\mu_B}'L$ maybe represented by Formula (3) shown below.

$$\overline{\mu_B}H - \overline{\mu_B}'L = (\overline{\mu_S}'\overline{\mu_B}' - \overline{\mu_S}'\overline{\mu_B}')t_S + (\overline{\mu_B}H_0 - \overline{\mu_B}'L_0) \quad (3)$$

In this manner, a difference signal, which represents a soft tissue image illustrating only the soft tissue and is free from the thickness of the bone, is capable of being obtained.

Also, in cases where L represented by Formula (1) shown above is multiplied by the factor of $\overline{\mu_S}'$, and H represented by Formula (2) shown above is multiplied by the factor of $\overline{\mu_S}$, the difference between $\overline{\mu_S}H$ and $\overline{\mu_S}'L$ may be represented by Formula (4) shown below.

$$\overline{\mu_S}H - \overline{\mu_S}'L = (\overline{\mu_S}'\overline{\mu_B} - \overline{\mu_S}\overline{\mu_B}')t_B + (\overline{\mu_S}H_0 - \overline{\mu_S}'L_0) \quad (4)$$

In this manner, a difference signal, which represents a bone image illustrating only the bone and is free from the thickness of the soft tissue, is capable of being obtained.

In each of Formula (3) and Formula (4) shown above, the mean attenuation coefficient, by which L is multiplied, and the mean attenuation coefficient, by which H is multiplied, act as the weight factors.

The mean attenuation coefficients, which are employed as the weight factors in each of Formula (3) and Formula (4) shown above, are determined by, for example, being presumed from the image signal having been obtained from the stimulable phosphor sheet, upon which the radiation having a low energy level impinged. Therefore, in cases where the energy subtraction processing is performed, an identical value of the mean attenuation coefficient is employed as the weight factor with respect to all of the pixels in each radiation image. However, the thickness of the substance contained in the object ((in cases where the object is the human body, the bone or the soft tissue) varies for different sites in the object. Also, as described above, the mean attenuation coefficient varies for different thicknesses of the substance contained in the object. Therefore, for example, in cases where the object is the human body, the thickness of the soft tissue or the thickness of the bone is not uniform in accordance with the site in the object. Accordingly, in cases where an identical value of the mean attenuation coefficient is employed as the weight factor with respect to all of the pixels in each radiation image, the problems occur in that an unnecessary structure pattern cannot be removed perfectly. As a result, the bone pattern remains unremoved in the soft tissue image, and the soft tissue pattern remains unremoved in the bone image.

SUMMARY OF THE INVENTION

The primary object of the present invention is to provide an energy subtraction processing method, wherein only a specific structure pattern contained in an object image is capable of being extracted accurately.

Another object of the present invention is to provide an apparatus for carrying out the energy subtraction processing method.

The specific object of the present invention is to provide a recording medium, on which a program for causing a computer to execute the energy subtraction processing method has been recorded and from which the computer is capable of reading the program.

As will be described later, in cases where a difference between logarithmic values of radiation doses at the time of formation of two radiation images is calculated, or a logarithmic value of a ratio between the radiation doses at the time of formation of two radiation images is calculated, a certain relationship is obtained between the difference between the logarithmic values of the radiation doses, or the logarithmic value of the ratio between the radiation doses, and the mean attenuation coefficient of a certain substance with respect to each of the two radiation images, which are associated with the calculation of the difference between the logarithmic values of the radiation doses or the calculation of the logarithmic value of the ratio between the radiation doses. In cases where the relationship described above is determined previously, if the difference between the logarithmic values of the radiation doses or the logarithmic value of the ratio between the radiation doses is found, the mean attenuation coefficient of the certain substance with respect to each of the two radiation images, which are associated with the calculation of the difference between the logarithmic values of the radiation doses or the calculation of the logarithmic value of the ratio between the radiation doses, will be capable of being calculated. A first energy subtraction processing method and a first energy subtraction processing apparatus in accordance with the present invention are based on such findings.

Specifically, the present invention provides a first energy subtraction processing method, comprising the steps of:

i) obtaining a plurality of image signals, each of which represents one of a plurality of radiation images of a single object and is made up of a series of image signal components, the plurality of the radiation images having been formed respectively with a plurality of kinds of radiation (such as X-rays or γ-rays) having different energy distributions and carrying image information of the object, different images of at least part of the object being embedded in the plurality of the radiation images, ii) weighting each of the image signals with a predetermined weight factor, and iii) performing a subtraction process on the image signal components of the weighted image signals, which image signal components represent corresponding pixels in the radiation images, a difference signal representing an image of a specific structure of the object being thereby obtained, wherein the improvement comprises the step of:

setting the predetermined weight factor with respect to each of pixels in each of the radiation images and in accordance with a difference between logarithmic values of radiation doses with respect to the corresponding pixels in the radiation images at the time of the formation of the plurality of the radiation images, or in accordance with a logarithmic value of a ratio between the radiation doses with respect to the corresponding pixels in the radiation images at the time of the formation of the plurality of the radiation images.

In order for the image signals representing the radiation images to be obtained, the plurality of kinds of the radiation having different energy distributions and carrying the image information of the object may be caused to impinge upon radiation detecting means, such as stimulable phosphor sheets or semiconductor sensors, and the image signals in accordance with the received radiation doses may be detected by the radiation detecting means. In cases where the radiation detecting means is constituted of the semiconductor sensors, a signal outputted from each of the semiconductor sensors may be taken as the image signal. In cases where the radiation detecting means is constituted of the stimulable phosphor sheets, in the same manner as that in the radiation image recording and reproducing systems described above, each of the stimulable phosphor sheets may be exposed to the stimulating rays, which cause the stimulable phosphor sheet to emit light in proportion to the amount of energy stored thereon during its exposure to the radiation, the emitted light may be photoelectrically detected, and the image signal may thereby be obtained. The formation of the plurality of the radiation images may be performed with the one-shot energy subtraction processing technique or the multi-shot energy subtraction processing technique.

The predetermined weight factor corresponds to each of the mean attenuation coefficients in Formula (3) or Formula (4) shown above. With respect to one radiation image, the same number of the mean attenuation coefficients as that of the kinds of the specific structures contained in the object are set. For example, in cases where the specific structures are the soft tissue and the bone of the human body, one mean attenuation coefficient of the soft tissue and one mean attenuation coefficient of the bone are obtained with respect to one radiation image. Therefore, in cases where three radiation images are to be processed, and the specific structures are the soft tissue and the bone of the human body, six kinds (=3×2) of the mean attenuation coefficients are obtained.

The term "radiation dose at the time of formation of a radiation image" as used herein means the dose of radiation, which carries the image information of the object and impinges upon the radiation detecting means when the image of the object is formed on the radiation detecting means. The radiation dose is capable of being obtained by directly detecting the radiation impinging upon the radiation detecting means. However, it is not always possible to detect the radiation dose with respect to each of the pixels in the radiation image. However, when the dose of radiation impinging upon the radiation detecting means is large, the image signal obtained from the radiation detecting means takes a large signal value. Thus the signal value of the image signal has the correspondence relationship with the radiation dose. Therefore, the image signal, which has been obtained from the radiation detecting means (and has not yet been subjected to image processing), should preferably be regarded as the radiation dose and utilized for the setting of the mean attenuation coefficient.

In cases where the radiation doses with respect to two radiation images are represented by $I1$ and $I2$, the relationship represented by the formula $\ln(I1)-\ln(I2)=\ln(I1/I2)$ is obtained. Therefore, the "difference between the logarithmic values of the radiation doses with respect to the corresponding pixels in the radiation images" and the "logarithmic value of the ratio between the radiation doses with respect to the corresponding pixels in the radiation images" take an identical value.

As for the relationship between the predetermined weight factor and the difference between the logarithmic values of the radiation doses with respect to the corresponding pixels in the radiation images, or the relationship between the predetermined weight factor and the logarithmic value of the ratio between the radiation doses with respect to the corresponding pixels in the radiation images, a table representing the relationship or a functional expression representing the relationship may be utilized. In cases where the table representing the relationship described above is utilized, reference may be made to the table, and the predetermined weight factor may thereby be set. In cases where the functional expression representing the relationship is utilized, operation processing may be performed with the functional expression, and the predetermined weight factor may thereby be set.

The relationship between the predetermined weight factor and the difference between the logarithmic values of the radiation doses describe above, or the relationship between the predetermined weight factor and the logarithmic value of the ratio between the radiation doses described above, varies for different image recording conditions employed in the image recording operation, such as the voltage of a radiation source, the kind of the radiation source, and the sensitivity of the radiation detecting means. Therefore, a plurality of tables or functions in accordance with various different image recording conditions should preferably be prepared previously, and a table or a function should preferably be selected in accordance with the image recording conditions. Also, the predetermined weight factor should preferably be set by the utilization of the thus selected table or the thus selected function.

The present invention also provides a first energy subtraction processing apparatus, comprising:

i) means for obtaining a plurality of image signals, each of which represents one of a plurality of radiation images of a single object and is made up of a series of image signal components, the plurality of the radiation images having been formed respectively with a plurality of kinds of radiation having different energy distributions and carrying image information of the object, different images of at least part of the object being embedded in the plurality of the radiation images, and ii) means for weighting each of the image signals with a predetermined weight factor, and performing a subtraction process on the image signal components of the weighted image signals, which image signal components represent corresponding pixels in the radiation images, in order to obtain a difference signal representing an image of a specific structure of the object, wherein the improvement comprises the provision of:

setting means for setting the predetermined weight factor with respect to each of pixels in each of the radiation images and in accordance with a difference between logarithmic values of radiation doses with respect to the corresponding pixels in the radiation images at the time of the formation of the plurality of the radiation images, or in accordance with a logarithmic value of a ratio between the radiation doses with respect to the corresponding pixels in the radiation images at the time of the formation of the plurality of the radiation images.

The first energy subtraction processing apparatus in accordance with the present invention should preferably be modified such that the apparatus further comprises storage means for storing information representing a table or a function, which represents a relationship between the predetermined weight factor and the difference between the logarithmic values of the radiation doses with respect to the corresponding pixels in the radiation images, or which represents a relationship between the predetermined weight factor and the logarithmic value of the ratio between the radiation doses with respect to the corresponding pixels in the radiation images, the relationship having been determined previously, and the setting means makes reference to the table or the function having been stored in the storage means and sets the predetermined weight factor.

In such cases, the first energy subtraction processing apparatus in accordance with the present invention should more preferably be modified such that the storage means stores a plurality of tables or functions, which represent the relationships having been set in accordance with various different image recording conditions at the time of formation of radiation images, and the setting means accepts selection of a table or a function in accordance with image recording conditions having been set at the time of the formation of the plurality of the radiation images, makes reference to the thus selected table or the thus selected function, and thereby sets the predetermined weight factor.

The present invention further provides a first recording medium, on which a program for causing a computer to execute the first energy subtraction processing method in accordance with the present invention has been recorded and from which the computer is capable of reading the program.

As described above, in cases where the difference between the logarithmic values of the radiation doses at the time of the formation of two radiation images is calculated, or the logarithmic value of the ratio between the radiation doses at the time of the formation of the two radiation images is calculated, a certain relationship is obtained between the difference between the logarithmic values of the radiation doses, or the logarithmic value of the ratio between the radiation doses, and the mean attenuation coefficient of a certain substance with respect to each of the two radiation images, which are associated with the calculation of the difference between the logarithmic values of the radiation doses or the calculation of the logarithmic value of the ratio between the radiation doses. In cases where the relationship described above is determined previously, if the difference between the logarithmic values of the radiation doses or the logarithmic value of the ratio between the radiation doses is found, the mean attenuation coefficient of the certain substance with respect to each of the two radiation images, which are associated with the calculation of the difference between the logarithmic values of the radiation doses or the calculation of the logarithmic value of the ratio between the radiation doses, will be capable of being calculated. Also, in cases where at least three radiation images are formed, the mean attenuation coefficient of a certain substance with respect to one of the at least three radiation images has a certain relationship with the difference between the logarithmic values of the radiation doses with respect to the other two radiation images, or with the logarithmic value of the ratio between the radiation doses with respect to the other two radiation images. Therefore, the mean attenuation coefficient of the certain substance with respect to the one radiation image is capable of being calculated in accordance with the difference between the logarithmic values of the radiation doses with respect to the other two radiation images, or in accordance with the logarithmic value of the ratio between the radiation doses with respect to the other two radiation images. Further, in the strict sense, the thus calculated mean attenuation coefficient deviates from a true value due to adverse effects of a noise and scattered radiation. A second energy subtraction processing method and a second energy subtraction processing apparatus in accordance with the present invention are based on such findings.

Specifically, the present invention still further provides a second energy subtraction processing method, comprising the steps of:

i) obtaining a plurality of image signals, each of which represents one of a plurality of, at least three, radiation images of a single object and is made up of a series of image signal components, the plurality of the radiation images having been formed respectively with a plurality of kinds of radiation (such as X-rays or γ-rays) having different energy distributions and carrying image information of the object, different images of at least part of the object being embedded in the plurality of the radiation images, ii) weighting each of two representative image signals, which are representative of the plurality of the image signals, with a predetermined weight factor, and iii) performing a subtraction process on the image signal components of the weighted image signals, which image signal components represent corresponding pixels in the two radiation images represented by the two representative image signals, a difference signal representing an image of a specific structure of the object being thereby obtained, wherein the improvement comprises the steps of:

a) setting a mean attenuation coefficient with respect to each of all of the radiation images, with respect to each of pixels in each of the radiation images, and in accordance with a difference between logarithmic values of radiation doses with respect to the corresponding pixels in the radiation images at the time of the formation of the plurality of the radiation images, or in accordance with a logarithmic value of a ratio between the radiation doses with respect to the corresponding pixels in the radiation images at the time of the formation of the plurality of the radiation images, the setting of the mean attenuation coefficient being performed for each of combinations of two radiation images, which two radiation images are associated with a calculation of the difference between the logarithmic values of the radiation doses or a calculation of the logarithmic value of the ratio between the radiation doses and are selected from the plurality of the radiation images, b) calculating a mean value of the mean attenuation coefficients, which have thus been set with respect to an identical radiation image among all of the radiation images and for all of the combinations of the two radiation images selected from the plurality of the radiation images, the mean value of the mean attenuation coefficients being calculated with respect to each of pixels in the identical radiation image, a plurality of mean values being obtained with respect to all of the radiation image, and c) setting representative values of the mean values, which representative values correspond to the radiation images represented by the two representative image signals, as the predetermined weight factors for the two representative image signals.

In the second energy subtraction processing method in accordance with the present invention, as in the first energy subtraction processing method in accordance with the present invention, in order for the image signals representing the radiation images to be obtained, the plurality of kinds of the radiation having different energy distributions and carrying the image information of the object may be caused to impinge upon the radiation detecting means, such as stimulable phosphor sheets or semiconductor sensors, and the image signals in accordance with the received radiation doses may be detected by the radiation detecting means. In cases where the radiation detecting means is constituted of the semiconductor sensors, a signal outputted from each of the semiconductor sensors may be taken as the image signal. In cases where the radiation detecting means is constituted of the stimulable phosphor sheets, in the same manner as that in the radiation image recording and reproducing systems described above, each of the stimulable phosphor sheets may be exposed to the stimulating rays, which cause the stimulable phosphor sheet to emit light in proportion to the amount of energy stored thereon during its exposure to the radiation, the emitted light may be photoelectrically detected, and the image signal may thereby be obtained. The formation of the plurality of the radiation images may be performed with the one-shot energy subtraction processing technique or the multi-shot energy subtraction processing technique.

In the second energy subtraction processing method in accordance with the present invention, the energy subtraction processing is performed on the two representative image signals, which are representative of the plurality of the image signals representing the plurality of (at least three) radiation images. In cases where the image recording operation is performed by utilizing at least three radiation detecting means, at least three image signals representing the radiation images are obtained in accordance with the at least three radiation detecting means. In such cases, as the two representative image signals, two arbitrary image signals selected from the at least three image signals may be employed.

Also, in cases where the stimulable phosphor sheet is employed as the radiation detecting means, a two-surface read-out technique may be employed, wherein the stimulating rays are irradiated to opposite surfaces of the stimulable phosphor sheet or only one surface of the stimulable phosphor sheet, and light emitted from one surface of the stimulable phosphor sheet and light emitted from the other surface of the stimulable phosphor sheet are detected photoelectrically. The two-surface read-out technique described above is described in, for example, U.S. Pat. No. 4,346,295. In cases where the two-surface read-out technique described above is employed, two image signals are obtained from one stimulable phosphor sheet. In the second energy subtraction processing method in accordance with the present invention, the two image signals having been obtained from one stimulable phosphor sheet with the two-surface read-out technique described above are also processed as the image signals representing two independent radiation images. In cases where the two-surface read-out technique described above is employed, a larger number of image signals than that of the radiation detecting means are obtained. In such cases, a mean signal value of the two image signals having been obtained from one stimulable phosphor sheet may be calculated and taken as one of the two representative image signals, which are representative of the plurality of the image signals.

The term "radiation dose at the time of formation of a radiation image" as used herein means the dose of radiation, which carries the image information of the object and impinges upon the radiation detecting means when the image of the object is formed on the radiation detecting means. The radiation dose is capable of being obtained by directly detecting the radiation impinging upon the radiation detecting means. However, it is not always possible to detect the radiation dose with respect to each of the pixels in the radiation image. However, when the dose of radiation impinging upon the radiation detecting means is large, the image signal obtained from the radiation detecting means takes a large signal value. Thus the signal value of the image signal has the correspondence relationship with the radiation dose. Therefore, in the second energy subtraction processing method in accordance with the present invention, as in the first energy subtraction processing method in accordance with the present invention, the image signal, which has been obtained from the radiation detecting means (and has not yet been subjected to image processing), should preferably be regarded as the radiation dose and utilized for the setting of the mean attenuation coefficient.

The mean attenuation coefficient is set for each of specific structures contained in the object. Therefore, with respect to one radiation image, the same number of the mean attenuation coefficients as that of the kinds of the specific structures contained in the object are set. For example, in cases where the specific structures are the soft tissue and the bone of the human body, one mean attenuation coefficient of the soft tissue and one mean attenuation coefficient of the bone are obtained with respect to one radiation image.

As will be described later, in cases where the difference between the logarithmic values of the radiation doses at the time of the formation of two radiation images is calculated, or the logarithmic value of the ratio between the radiation doses at the time of the formation of the two radiation images is calculated, a certain relationship is obtained between the difference between the logarithmic values of the radiation doses, or the logarithmic value of the ratio between the radiation doses, and the mean attenuation coefficient of a certain substance with respect to each of the two radiation images, which are associated with the calculation of the difference between the logarithmic values of the radiation doses or the calculation of the logarithmic value of the ratio between the radiation doses. Also, in cases where at least three radiation images are formed, the mean attenuation coefficient of a certain substance with respect to one of the at least three radiation images has a certain relationship with the difference between the logarithmic values of the radiation doses with respect to the other two radiation images, or with the logarithmic value of the ratio between the radiation doses with respect to the other two radiation images. Therefore, the mean attenuation coefficient of the certain substance with respect to the one radiation image is capable of being calculated in accordance with the difference between the logarithmic values of the radiation doses with respect to the other two radiation images, or in accordance with the logarithmic value of the ratio between the radiation doses with respect to the other two radiation images. Accordingly, for each of the combinations of the two radiation images, which two radiation images are associated with the calculation of the difference between the logarithmic values of the radiation doses or the calculation of the logarithmic value of the ratio between the radiation doses and are selected from the plurality of the radiation images, the mean attenuation coefficients with respect to all of the radiation images are capable of being set.

For example, in cases where the specific structures are the soft tissue and the bone of the human body, and three radiation images are to be processed, with respect to each of the specific structures, there are three kinds of the combinations of the two radiation images, which two radiation images are associated with the calculation of the difference between the logarithmic values of the radiation doses or the calculation of the logarithmic value of the ratio between the radiation doses. Therefore, for each of the three kinds of the combinations, the mean attenuation coefficients with respect to all of the radiation images (i.e., with respect to the three radiation images) are set. Also, for one radiation image, the mean attenuation coefficient is set for each of the soft tissue and the bone. Accordingly, in such cases, 18 kinds [=the number of the combinations (3)×the number of the radiation images (3)×the number of the specific structures (2)] of the mean attenuation coefficients are set.

The mean value of the mean attenuation coefficients, which have been set with respect to the identical radiation image among all of the radiation images and for all of the combinations of the two radiation images selected from the plurality of the radiation images, is calculated with respect to each of the radiation images and with respect to each of the specific structures contained in the object. For example, in cases where the number of the radiation images is three, as the mean value of the mean attenuation coefficients, which have been set with respect to the identical radiation image, three mean values are calculated for the three radiation images and with respect to each of the specific structures contained in the object. Therefore, in cases where three radiation images are to be processed, and the specific structures are the soft tissue and the bone of the human body, six kinds (=3×2) of the mean values are obtained.

The mean value described above may be a simple arithmetic mean value. However, it is considered that, due to adverse effects of a noise contained in the radiation, scattered radiation, and the like, the mean attenuation coefficient deviates from a true value, i.e. the value which will be obtained in cases where the noise, the scattered radiation, and the like, are not contained in the radiation. Also, it is considered that the deviation of the mean attenuation coefficient occurs in the normal distribution. Therefore, the mean value of the mean attenuation coefficients described above should preferably be calculated with a weighted mean calculating process, in which the mean attenuation coefficients are weighted in accordance with standard deviations of the mean attenuation coefficients.

In the second energy subtraction processing method in accordance with the present invention, the difference signal is obtained from the two representative image signals, which are representative of the plurality of the image signals representing the plurality of the radiation images. As described above, in cases where the image recording operation is performed by utilizing at least three radiation detecting means, at least three image signals representing the radiation images are obtained in accordance with the at least three radiation detecting means. In such cases, two arbitrary image signals are selected as the two representative image signals from the at least three image signals and subjected to the energy subtraction processing. In such cases, as the representative values of the mean values, the mean values, which have been calculated with respect to the radiation images represented by the two representative image signals having been selected, are employed.

Also, in cases where the stimulable phosphor sheet is employed as the radiation detecting means, and the two-surface read-out technique described above are employed, the mean signal value of the two image signals having been obtained from one stimulable phosphor sheet may be calculated and taken as one of the two representative image signals, which are representative of the plurality of the image signals. In such cases, as one of the representative values of the mean values, the value obtained by averaging the mean values having been calculated with respect to the radiation images represented by the two image signals, from which the mean signal value has been calculated, may be employed.

As described above, in cases where the radiation doses with respect to two radiation images are represented by I1 and I2, the relationship represented by the formula $\ln(I1)-\ln(I2)=\ln(I1/I2)$ is obtained. Therefore, the "difference between the logarithmic values of the radiation doses with respect to the corresponding pixels in the radiation images" and the "logarithmic value of the ratio between the radiation doses with respect to the corresponding pixels in the radiation images" take an identical value.

As for the relationship between the mean attenuation coefficient and the difference between the logarithmic values of the radiation doses with respect to the corresponding pixels in the radiation images, or the relationship between the predetermined weight factor and the logarithmic value of the ratio between the radiation doses with respect to the corresponding pixels in the radiation images, a table representing the relationship or a functional expression representing the relationship may be utilized. In cases where the table representing the relationship described above is utilized, reference may be made to the table, and the mean attenuation coefficient may thereby be set. In cases where the functional expression representing the relationship is utilized, operation processing may be performed with the functional expression, and the mean attenuation coefficient may thereby be set.

The relationship between the mean attenuation coefficient and the difference between the logarithmic values of the radiation doses describe above, or the relationship between the mean attenuation coefficient and the logarithmic value of the ratio between the radiation doses described above, varies for different image recording conditions employed in the image recording operation, such as the voltage of a radiation source, the kind of the radiation source, and the sensitivity of the radiation detecting means. Therefore, a plurality of tables or functions in accordance with various different image recording conditions should preferably be prepared previously, and a table or a function should preferably be selected in accordance with the image recording conditions. Also, the mean attenuation coefficient should preferably be set by the utilization of the thus selected table or the thus selected function.

As described above, in the second energy subtraction processing method in accordance with the present invention, the mean value of the mean attenuation coefficients should preferably be calculated with a weighted mean calculating process, in which the mean attenuation coefficients are weighted in accordance with standard deviations of the mean attenuation coefficients.

In such cases, the weighting of each of the mean attenuation coefficients having been set in accordance with a radiation image, which contains more of scattered radiation than the other radiation images among the plurality of the radiation images, should preferably be set to be lighter than the weighting of the mean attenuation coefficient having been set in accordance with the other radiation images.

By way of example, in cases where the plurality of the radiation images are formed with the one-shot energy subtraction processing technique, the radiation image, which has been obtained with the radiation detecting means located at a position close to the object, contains more of the scattered radiation than the radiation images, which have been obtained with the radiation detecting means located at positions remote from the object. Therefore, in such cases, the term "radiation image containing more of scattered radiation than the other radiation images" as used herein means the radiation image, which has been obtained with the radiation detecting means located at the position closest to the object.

In cases where the thickness of the object is large, much of scattered radiation occurs. Also, in cases where the thickness of the object is large, the dose of the radiation impinging upon the radiation detecting means becomes small. Therefore, in the second energy subtraction processing method in accordance with the present invention, with respect to the radiation image, which contains more of the scattered radiation than the other radiation images, the weighting of each of the mean attenuation coefficients having been set in accordance with the radiation image should preferably be set to be light in cases where the radiation dose is small.

The present invention also provides a second energy subtraction processing apparatus, comprising:
  i) means for obtaining a plurality of image signals, each of which represents one of a plurality of, at least three, radiation images of a single object and is made up of a series of image signal components, the plurality of the radiation images having been formed respectively with a plurality of kinds of radiation having different energy distributions and carrying image information of the object, different images of at least part of the object being embedded in the plurality of the radiation images, and
  ii) means for weighting each of two representative image signals, which are representative of the plurality of the image signals, with a predetermined weight factor, and performing a subtraction process on the image signal components of the weighted image signals, which image signal components represent corresponding pixels in the two radiation images represented by the two representative image signals, in order to obtain a difference signal representing an image of a specific structure of the object,
  wherein the, improvement comprises the provision of:
  a) mean attenuation coefficient setting means for setting a mean attenuation coefficient with respect to each of all of the radiation images, with respect to each of pixels in each of the radiation images, and in accordance with a difference between logarithmic values of radiation doses with respect to the corresponding pixels in the radiation images at the time of the formation of the plurality of the radiation images, or in accordance with a logarithmic value of a ratio between the radiation doses with respect to the corresponding pixels in the radiation images at the time of the formation of the plurality of the radiation images, the setting of the mean attenuation coefficient being performed for each of combinations of two radiation images, which two radiation images are associated with a calculation of the difference between the logarithmic values of the radiation doses or a calculation of the logarithmic value of the ratio between the radiation doses and are selected from the plurality of the radiation images,
  b) mean value calculating means for calculating a mean value of the mean attenuation coefficients, which have thus been set with respect to an identical radiation image among all of the radiation images and for all of the combinations of the two radiation images selected from the plurality of the radiation images, the mean value of the mean attenuation coefficients being calculated with respect to each of pixels in the identical radiation image, a plurality of mean values being obtained with respect to all of the radiation image, and
  c) setting means for setting representative values of the mean values, which representative values correspond to the radiation images represented by the two representative image signals, as the predetermined weight factors for the two representative image signals.

The second energy subtraction processing apparatus in accordance with the present invention should preferably be modified such that the apparatus further comprises storage means for storing information representing a table or a function, which represents a relationship between the mean attenuation coefficient and the difference between the logarithmic values of the radiation doses with respect to the corresponding pixels in the radiation images, or which represents a relationship between the mean attenuation coefficient and the logarithmic value of the ratio between the radiation doses with respect to the corresponding pixels in the radiation images, the relationship having been determined previously, and
  the mean attenuation coefficient setting means makes reference to the table or the function having been stored in the storage means and sets the mean attenuation coefficient.

In such cases, the second energy subtraction processing apparatus in accordance with the present invention should more preferably be modified such that the storage means stores a plurality of tables or functions, which represent the relationships having been set in accordance with various different image recording conditions at the time of formation of radiation images, and
  the mean attenuation coefficient setting means accepts selection of a table or a function in accordance with image recording conditions :having been set at the time of the formation of the plurality of the radiation images, makes reference to the thus selected table or the thus selected function, and thereby sets the mean attenuation coefficient.

In the second energy subtraction processing apparatus in accordance with the present invention, the mean value calculating means should preferably be means for calculating the mean value of the mean attenuation coefficients with a weighted mean calculating process, in which the mean attenuation coefficients are weighted in accordance with standard deviations of the mean attenuation coefficients.

In such cases, the mean value calculating means should preferably set the weighting of each of the mean attenuation coefficients having been set in accordance with a radiation image, which contains more of scattered radiation than the other radiation images among the plurality of the radiation images, to be lighter than the weighting of the mean attenuation coefficient having been set in accordance with the other radiation images.

Also, in such cases, in the second energy subtraction processing apparatus in accordance with the present invention, the mean value calculating means should preferably operate such that, with respect to the radiation image, which contains more of the scattered radiation than the other radiation images, the weighting of each of the mean attenuation coefficients having been set in accordance with the radiation image is set to be light in cases where the radiation dose is small.

The present invention further provides a second recording medium, on which a program for causing a computer to execute the second energy subtraction processing method in accordance with the present invention has been recorded and from which the computer is capable of reading the program.

The first energy subtraction processing method and the first energy subtraction processing apparatus in accordance with the present invention are based on the findings that the certain relationship is obtained between the difference between the logarithmic values of the radiation doses with respect to the radiation images, or the logarithmic value of the ratio between the radiation doses with respect to the radiation images, and the mean attenuation coefficient, i.e. the weight factor. With the first energy subtraction processing method and the first energy subtraction processing apparatus in accordance with the present invention, on the basis of the findings described above, the predetermined weight factor is set with respect to each of the pixels in each of the radiation images and in accordance with the difference between the logarithmic values of the radiation doses with respect to the corresponding pixels in the radiation images at the time of the formation of the plurality of the radiation images, or in accordance with the logarithmic value of the ratio between the radiation doses with respect to the corresponding pixels in the radiation images at the time of the formation of the plurality of the radiation images. The radiation dose with respect to each of the pixels in each of the radiation images varies in accordance with the thickness of the specific structure contained in the object. Therefore, the predetermined weight factor, which has been set with respect to each of the pixels in each of the radiation images and in accordance with the difference between the logarithmic values of the radiation doses with respect to the corresponding pixels in the radiation images, or in accordance with the logarithmic value of the ratio between the radiation doses with respect to the corresponding pixels in the radiation images, takes a value in accordance with the thickness of the specific structure. Accordingly, in cases where the image signals are multiplied by the predetermined weight factors, which have thus been set, and the thus weighted image signals are subtracted from each other, regardless of the thickness of the structure contained in the object, a pattern of an unnecessary structure is capable of being removed approximately perfectly. As a result, the difference signal representing an image, in which only a pattern of the specific structure is illustrated accurately, is capable of being obtained.

Also, with the first energy subtraction processing method and the first energy subtraction processing apparatus in accordance with the present invention, the table or the function, which represents the relationship between the predetermined weight factor and the difference between the logarithmic values of the radiation doses, or which represents the relationship between the predetermined weight factor and the logarithmic value of the ratio between the radiation doses, may be determined previously. In such cases, reference may be made to the table or the function, and the predetermined weight factor is capable of being set easily. Therefore, the calculation of the difference signal is capable of being made efficiently.

Further, with the first energy subtraction processing method and the first energy subtraction processing apparatus in accordance with the present invention, the plurality of the tables or the functions, which represent the relationships having been set in accordance with various different image recording conditions, may be prepared previously. Also, a table or a function may be selected in accordance with the image recording conditions having been set at the time of the formation of the plurality of the radiation images. Reference may be made to the thus selected table or the thus selected function, and the predetermined weight factor may thereby be set. In such cases, only the pattern of the specific structure is capable of being extracted accurately regardless of the image recording conditions.

The second energy subtraction processing method and the second energy subtraction processing apparatus in accordance with the present invention are based on the findings that the certain relationship is obtained between the difference between the logarithmic values of the radiation doses with respect to the radiation images, or the logarithmic value of the ratio between the radiation doses with respect to the radiation images, and the mean attenuation coefficient of a certain substance with respect to each of the two radiation images, which are associated with the calculation of the difference between the logarithmic values of the radiation doses or the calculation of the logarithmic value of the ratio between the radiation doses. With the second energy subtraction processing method and the second energy subtraction processing apparatus in accordance with the present invention, on the basis of the findings described above, in accordance with the difference between the logarithmic values of the radiation doses with respect to the radiation images, or in accordance with the logarithmic value of the ratio between the radiation doses with respect to the radiation images, the mean attenuation coefficient is calculated for each of the combinations of the two radiation images, which two radiation images are associated with the calculation of the difference between the logarithmic values of the radiation doses or the calculation of the logarithmic value of the ratio between the radiation doses. Specifically, the mean attenuation coefficient is set with respect to each of all of the radiation images, and the setting of the mean attenuation coefficient is performed for each of the combinations of the two radiation images, which two radiation images are associated with the calculation of the difference between the logarithmic values of the radiation doses or the calculation of the logarithmic value of the ratio between the radiation doses. Also, a calculation is made to find the mean value of the mean attenuation coefficients, which have thus been set with respect to an identical radiation image among all of the radiation images and for all of the combinations of the two radiation images selected from the plurality of the radiation images. The mean value of the mean attenuation coefficients is calculated with respect to each of the pixels in the identical radiation image. A plurality of the mean values are thus obtained with respect to all of the radiation image. Further, the representative values of the mean values, which representative values correspond to the radiation images represented by the two representative image signals to be subjected to the energy subtraction processing, are determined. The thus determined representative values are set as the predetermined weight factors for the two representative image signals, and the energy subtraction processing is performed by the utilization of the predetermined weight factors.

Therefore, in cases where the image signals are multiplied by the predetermined weight factors, which have thus been set, and the thus weighted image signals are subtracted from each other, regardless of the thickness of the structure contained in the object, a pattern of an unnecessary structure is capable of being removed approximately perfectly. As a result, the difference signal representing an image, in which only a pattern of the specific structure is illustrated accurately, is capable of being obtained.

As described above, in the strict sense, the mean attenuation coefficient deviates from the true value due to adverse effects of the noise and the scattered radiation. However, with the second energy subtraction processing method and the second energy subtraction processing apparatus in accordance with the present invention, the plurality of the mean attenuation coefficients are calculated with respect to each of the radiation images, and the mean value of the mean attenuation coefficients is calculated with respect to each radiation image. Also, the representative values of the thus calculated mean values are set as the predetermined weight factors in the energy subtraction processing. Therefore, the mean attenuation coefficients comparatively close to the true values are capable of being utilized in the energy subtraction processing. Accordingly, the pattern of the specific structure is capable of being extracted accurately.

Also, with the second energy subtraction processing method and the second energy subtraction processing apparatus in accordance with the present invention, the table or the function, which represents the relationship between the mean attenuation coefficient and the difference between the logarithmic values of the radiation doses, or which represents the relationship between the mean attenuation coefficient and the logarithmic value of the ratio between the radiation doses, may be determined previously. In such cases, reference may be made to the table or the function, and the mean attenuation coefficient is capable of being set easily. Therefore, the calculation of the difference signal is capable of being made efficiently.

Further, with the second energy subtraction processing method and the second energy subtraction processing apparatus in accordance with the present invention, the plurality of the tables or the functions, which represent the relationships having been set in accordance with various different image recording conditions, may be prepared previously. Also, a table or a function may be selected in accordance with the image recording conditions having been set at the time of the formation of the plurality of the radiation images. Reference may be made to the thus selected table or the thus selected function, and the mean attenuation coefficient may thereby be set. In such cases, only the pattern of the specific structure is capable of being extracted accurately regardless of the image recording conditions.

Furthermore, it is considered that the deviation of the mean attenuation coefficient from the true value occurs in the normal distribution. Therefore, with the second energy subtraction processing method and the second energy subtraction processing apparatus in accordance with the present invention, the mean value of the mean attenuation coefficients described above may be calculated with the weighted mean calculating process, in which the mean attenuation coefficients are weighted in accordance with the standard deviations of the mean attenuation coefficients. In such cases, the predetermined weight factors are capable of being set accurately.

Also, deviations of the mean attenuation coefficients having been set in accordance with a radiation image, which contains much of the scattered radiation, from the true values are large due to the adverse effects of the scattered radiation. Therefore, with the second energy subtraction processing method and the second energy subtraction processing apparatus in accordance with the present invention, the weighting of each of the mean attenuation coefficients, which have been set in accordance with a radiation image containing more of scattered radiation than the other radiation images among the plurality of the radiation images, in accordance with the standard deviations of the mean attenuation coefficients may be set to be lighter than the weighting of the mean attenuation coefficient having been set in accordance with the other radiation images. In such cases, the effects of the mean attenuation coefficients, which deviate largely from the true values due to the scattered radiation, are capable of being suppressed. Therefore, the predetermined weight factors are capable of being set more accurately.

Further, in cases where the thickness of the object is large, the radiation dose becomes small, and the amount of the scattered radiation becomes large. Therefore, in the second energy subtraction processing method in accordance with the present invention, with respect to the radiation image, which contains more of the scattered radiation than the other radiation images, the weighting of each of the mean attenuation coefficients, which have been set in accordance with the radiation image, in accordance with the standard deviations of the mean attenuation coefficients may be set to be light in cases where the radiation dose is small. In such cases, the adverse effects of the scattered radiation are capable of being minimized.

BRIEF DESCRIPTION OF THE DRAWINGS

FIG. 2 is a perspective view showing a radiation image read-out apparatus, in which a first embodiment of the energy subtraction processing apparatus in accordance with the present invention is employed.

FIG. 8 is a perspective view showing a radiation image read-out apparatus, in which a third embodiment of the energy subtraction processing apparatus in accordance with the present invention is employed, FIG. 9 is an explanatory view showing how setting means is constituted and how processing in the setting means is performed, FIG. 10 is a graph showing a relationship between the logarithmic radiation dose difference, which is calculated for each of combinations of two stimulable phosphor sheets among stimulable phosphor sheets IP1, IP2, and IP3, and the mean attenuation coefficient with respect to a certain stimulable phosphor sheet, which relationship has been determined experimentally by the inventors.

DESCRIPTION OF THE PREFERRED EMBODIMENTS

The present invention will hereinbelow be described in further detail with reference to the accompanying drawings.

Figure 1:
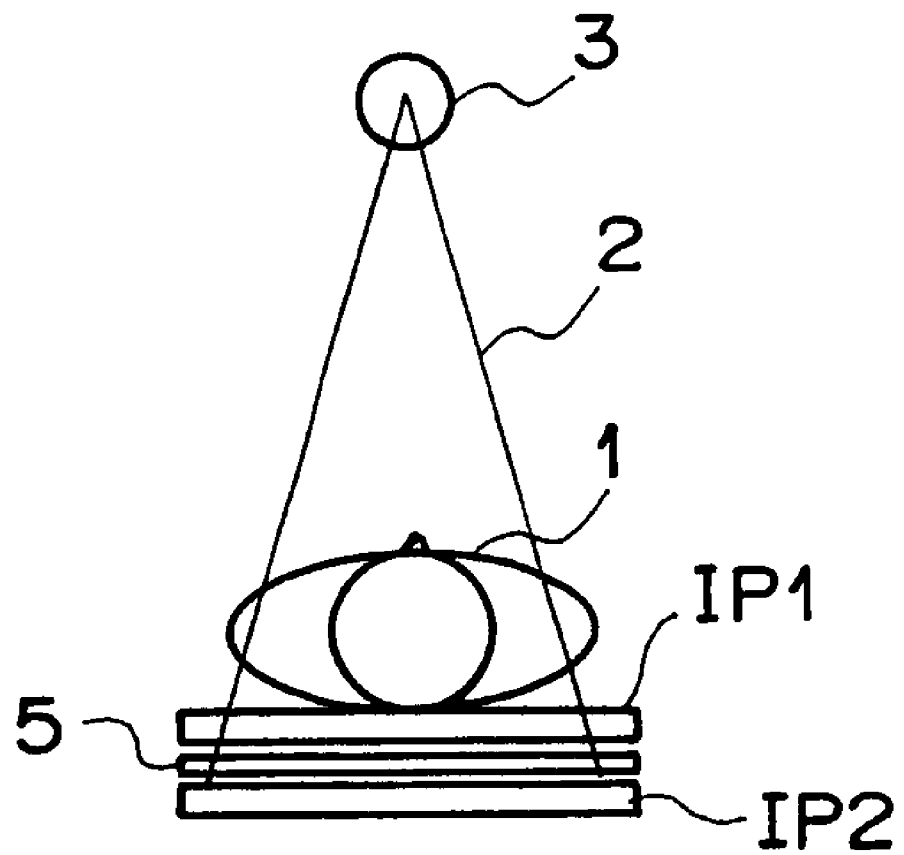
FIG. 1 is a schematic view showing an example of how radiation images are recorded on stimulable phosphor sheets.

FIG. 1 shows an example of a radiation image recording apparatus for performing a one-shot energy subtraction processing technique, in which radiation 2 carrying image information of an object 1 is irradiated simultaneously to a first stimulable phosphor sheet IP1 and a second stimulable phosphor sheet IP2 such that the two stimulable phosphor sheets IP1 and IP2 are exposed respectively to two kinds of radiation having different energy distributions. As illustrated in FIG. 1, the first stimulable phosphor sheet IP1 is located at a position close to a radiation source 3 for producing the radiation 2, and the second stimulable phosphor sheet IP2 is located at a position remote from the radiation source 3 and with a slight spacing from the first stimulable phosphor sheet IP1. Also, a radiation energy converting filter 5, which may be constituted of a copper plate, is located between the: first stimulable phosphor sheet IP1 and the second stimulable phosphor sheet IP2. In this state, the radiation source 3 is driven. As a result, a radiation image of the object 1 is formed on the first stimulable phosphor sheet IP1 and with the radiation 2 having a low energy level and containing the so-called "soft rays." Also, a radiation image of the object 1 is formed on the second stimulable phosphor sheet IP2 and with the radiation 2, which has a high energy level and from which the soft rays have been removed. At this time, the relationship between the position of the object 1 and the position of the first stimulable phosphor sheet IP1, and the relationship between the position of the object 1 and the position of the second stimulable phosphor sheet IP2 are identical with each other. In this manner, two radiation images, in which different images of at least part of the object 1 are embedded, are stored respectively on the two stimulable phosphor sheets IP1 and IP2.

FIG. 2 is a perspective view showing a radiation image read-out apparatus, in which a first embodiment of the energy subtraction processing apparatus in accordance with the present invention is employed. With reference to FIG. 2, of the two stimulable phosphor sheets IP1 and IP2, on which the radiation images of the object 1 have been stored, the first stimulable phosphor sheet IP1 is firstly set on an endless belt 9. The first stimulable phosphor sheet IP1 is moved by the endless belt 9 in the sub-scanning direction indicated by the arrow Y. At the same time, a laser beam 11, which serves as stimulating rays, is produced by a laser beam source 10. The laser beam 11 is deflected by a scanning mirror 12' and caused to scan the first stimulable phosphor sheet IP1 in the main scanning directions indicated by the double-headed arrow X. When the first stimulable phosphor sheet IP1 is exposed to the laser beam 11, the first stimulable phosphor sheet IP1 emits light 13 in proportion to the amount of energy stored thereon during its exposure to the radiation 2. The emitted light 13 enters into a light guide member 14, which is made from a transparent acrylic plate, from one end face of the light guide member 14. The emitted light 13 is guided through repeated total reflection inside of the light guide member 14 and detected by a photomultiplier 15. The photomultiplier 15 generates an analog output signal Q1 corresponding to the intensity of the emitted light 13, i.e. representing the radiation image having been stored on the first stimulable phosphor sheet IP1.

The output signal Q1 is logarithmically converted by a logarithmic converter 16 and is then converted by an analog-to-digital converter 17 into a digital image signal S1. Thereafter, the radiation image having been stored on the second stimulable phosphor sheet IP2 is read out in the same manner as that described above, and an output signal Q2 representing the radiation image is thereby obtained. The output signal Q2 is logarithmically converted by the logarithmic converter 16 and is then converted by the analog-to-digital converter 17 into a digital image signal S2.

The image signal S1 and the image signal S2 are fed into subtraction processing means 18. In the subtraction processing means 18, energy subtraction processing is performed on the image signal S1 and the image signal S2. From the energy subtraction processing, a difference signal $S_S$ representing a soft tissue image, in which only a pattern of a soft tissue contained in the object 1 is illustrated, and a difference signal $S_B$ representing a bone image, in which only a pattern of a bone contained in the object 1 is illustrated, are obtained. Weight factors for the image signals S1 and S2, which weight factors are to be utilized for the energy subtraction processing, are set by setting means 19. The setting means 19 makes reference to a table T having been stored in storage means 20 and sets the weight factors. How the weight factors are set will be described hereinbelow.

In the subtraction processing means 18, the energy subtraction processing is performed with Formula (5) shown below, and the difference signal $S_S$ representing the soft tissue image, in which only the pattern of the soft tissue contained in the object 1 is illustrated, is obtained. Also, the energy subtraction processing is performed with Formula (6) shown below, and the difference signal $S_B$ representing the bone image, in which only the pattern of the bone contained in the object is illustrated, is obtained.

$$S_S = \overline{\mu_B}S2 - \overline{\mu_B}'S1 = (\overline{\mu_S}\overline{\mu_B}' - \overline{\mu_S}'\overline{\mu_B})t_S + (\overline{\mu_B}I2_0 - \overline{\mu_B}'I1_0) \tag{5}$$

$$S_B = \overline{\mu_S}S2 - \overline{\mu_S}'S1 = (\overline{\mu_S}'\overline{\mu_B} - \overline{\mu_S}\overline{\mu_B}')t_B + (\overline{\mu_S}I2_0 - \overline{\mu_S}'I1_0) \tag{6}$$

wherein $\overline{\mu_B}$ represents the mean attenuation coefficient of the bone with respect to the first stimulable phosphor sheet IP1, $\overline{\mu_S}$ represents the mean attenuation coefficient of the soft tissue with respect to the first stimulable phosphor sheet IP1, $\overline{\mu_S}'$ represents the mean attenuation coefficient of the bone with respect to the second stimulable phosphor sheet IP2, $\overline{\mu_S}'$ represents the mean attenuation coefficient of the soft tissue with respect to the second stimulable phosphor sheet IP2, $t_S$ represents the thickness of the bone, $t_B$ represents the thickness of the soft tissue, and each of $I1_0$ and $I2_0$ represents the fixed number depending upon the radiation source.

In Formula (5) and Formula (6), the mean attenuation coefficients, by which the image signals S1 and S2 are multiplied, act as the weight factors.

A substance has a radiation attenuation coefficient depending upon radiation energy. Also, in cases where the radiation irradiated to the object is not monochromatic and is distributed over a certain energy range, the energy distribution of the radiation impinging upon each of the first stimulable phosphor sheet IP1 and the second stimulable phosphor sheet IP2 changes depending upon the thickness of a substance (i.e., the bone or the soft tissue) contained in the object. Such a phenomenon is referred to as the beam hardening. Therefore, in this embodiment, the radiation attenuation coefficient of the substance is weighted with the energy distribution of the detected radiation (i.e., the radiation having impinged upon the stimulable phosphor sheet) and averaged. The thus obtained value is defined as the mean attenuation coefficient. Accordingly, the mean attenuation coefficient varies for different thicknesses of the substance.

Figure 3A:
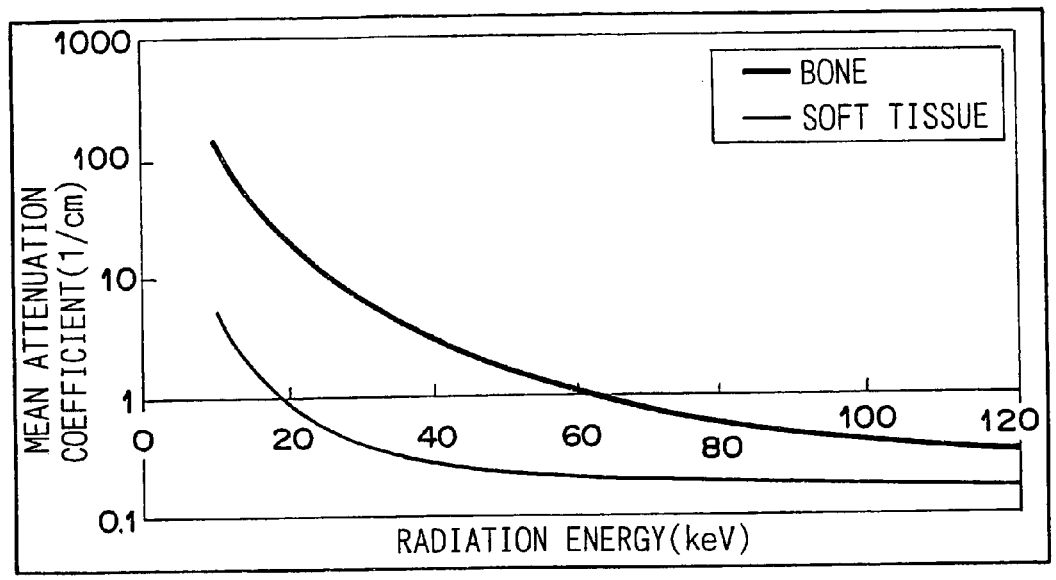
FIG. 3A is a graph showing a relationship between radiation energy and mean attenuation coefficients of a bone and a soft tissue of a human body.
Figure 3B:
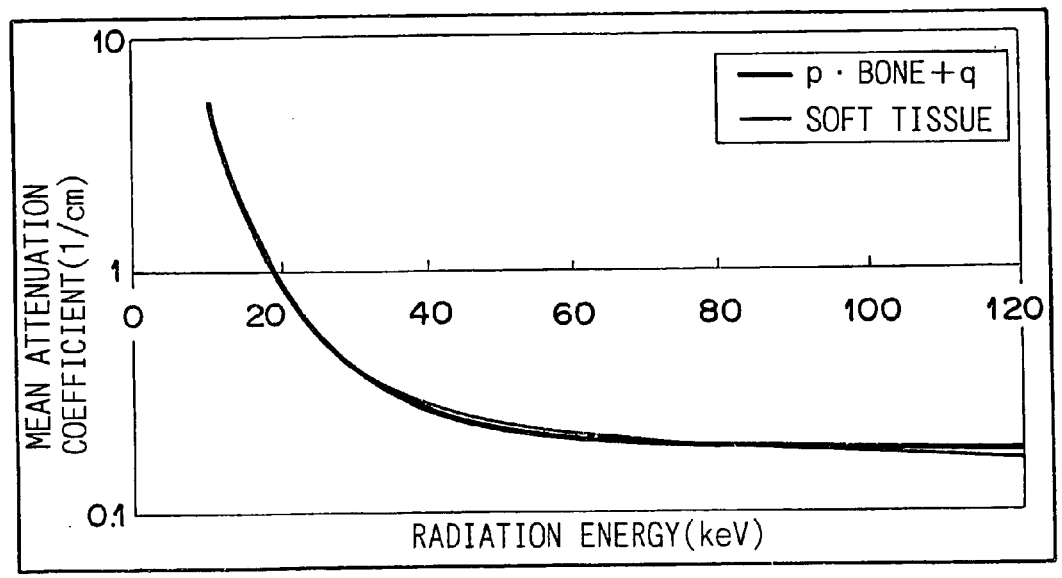
FIG. 3B is a graph showing how the mean attenuation coefficient of the soft tissue is capable of being approximately represented with the mean attenuation coefficient of the bone.

As for each of substances (e.g., the bone and the soft tissue of the human body) having the characteristics such that the mean attenuation coefficient decreases smoothly with respect to radiation energy, the relationship between the radiation energy of the radiation, which has passed through each substance, and the mean attenuation coefficient of the substance is capable of being approximately represented by a simple formula. For example, the relationship indicated by the upper curve in FIG. 3A is obtained between the radiation energy and mean attenuation coefficient of the bone of the human body. Also, the relationship indicated by the lower curve in FIG. 3A is obtained between the radiation energy and mean attenuation coefficient of the soft tissue of the human body. FIG. 3B is a graph showing how the mean attenuation coefficient of the soft tissue is capable of being approximately represented with the mean attenuation coefficient of the bone. As illustrated in FIG. 3B, in cases where the mean attenuation coefficient of the bone is multiplied by a fixed number, p, and a fixed number, q (q>0), is added to the thus obtained product, the mean attenuation coefficient of the soft tissue is capable of being approximately represented with the mean attenuation coefficient of the bone. The approximate representation is represented by Formula (7) shown below. In this embodiment, the character "S" attached to the mean attenuation coefficient represents the soft tissue, and the character "B" attached to the mean attenuation coefficient represents the bone.

$$\overline{\mu_S} = p\overline{\mu_B} + q \tag{7}$$

Also, in cases where the mean attenuation coefficient of the soft tissue is multiplied by a fixed number, p', and a fixed number, q' (q'>0), is added to the thus obtained product, the mean attenuation coefficient of the bone is capable of being approximately represented with the mean attenuation coefficient of the soft tissue. The approximate representation is represented by Formula (8) shown below.

$$\overline{\mu_B} = p'\overline{\mu_S} + q' \tag{8}$$

In cases where the energy distribution of the radiation 2 produced by the radiation source 3 is represented by S(E), and the sensitivity of the first stimulable phosphor sheet IP1 and the second stimulable phosphor sheet IP2 with respect to the radiation energy is represented by D(E), an energy distribution I1(E) of the radiation impinging upon the first stimulable phosphor sheet IP1 may be represented by Formula (9) shown below. Also, an energy distribution I2(E) of the radiation impinging upon the second stimulable phosphor sheet IP2 may be represented by Formula (10) shown below.

$$I1(E) = S(E)D(E)\exp[-\mu_S(E)t_S - \mu_B(E)t_B] \tag{9}$$

$$I2(E) = S(E)\exp[-\mu_{IP}(E)t_{IP} - \mu_{Cu}(E)t_{Cu}] \cdot D(E)\exp[-\mu_S(E)t_S - \mu_B(E)t_B] \tag{10}$$

wherein $\mu_S(E)$ represents the radiation attenuation coefficient of the soft tissue, $\mu_B(E)$ represents the radiation attenuation coefficient of the bone, $\mu_{IP}(E)$ represents the radiation attenuation coefficient of the stimulable phosphor sheet, $\mu_{Cu}(E)$ represents the radiation attenuation coefficient of the radiation energy converting filter, $t_{IP}$ represents the thickness of the stimulable phosphor sheet, and $t_{Cu}$ represents the thickness of the radiation energy converting filter.

In cases where S(E)D(E) in Formula (9) is replaced by A(E), and $S(E)\exp[-\mu_{IP}(E)t_{IP} - \mu_{Cu}(E)t_{Cu}]D(E)$ in Formula (10) is replaced by B(E), a radiation dose I1 of the radiation impinging upon the first stimulable phosphor sheet IP1 may be represented by Formula (11) shown below, and a radiation dose I2 of the radiation impinging upon the second stimulable phosphor sheet IP2 may be represented by Formula (12) shown below.

$$I1 = \int I1(E)dE = \int A(E)\exp[-\mu_S(E)t_S - \mu_B(E)t_B]dE \tag{11}$$

$$I2 = \int I2(E)dE = \int B(E)\exp[-\mu_S(E)t_S - \mu_B(E)t_B]dE \tag{12}$$

The integration is performed with respect to the entire energy range of the radiation.

As described above, the mean attenuation coefficient is defined as a value obtained from the calculation, in which the radiation attenuation coefficient of a substance is weighted with the energy distribution of the detected radiation and averaged. Therefore, the mean attenuation coefficient of the soft tissue with respect to the first stimulable phosphor sheet IP1 may be represented by Formula (13) shown below. Also, the mean attenuation coefficient of the bone with respect to the first stimulable phosphor sheet IP1 may be represented by Formula (14) shown below.

$$\overline{\mu_S} = \frac{\int \mu_S(E)I1(E)dE}{\int I1(E)dE} \quad (13)$$

$$= \frac{\int \mu_S(E)A(E)\exp[-\mu_S(E)t_S - \mu_B(E)t_B]dE}{\int A(E)\exp[-\mu_S(E)t_S - \mu_B(E)t_B]dE}$$

$$\overline{\mu_B} = \frac{\int \mu_B(E)I1(E)dE}{\int I1(E)dE} \quad (14)$$

$$= \frac{\int \mu_B(E)A(E)\exp[-\mu_S(E)t_S - \mu_B(E)t_B]dE}{\int A(E)\exp[-\mu_S(E)t_S - \mu_B(E)t_B]dE}$$

Further, the mean attenuation coefficient of the soft tissue with respect to the second stimulable phosphor sheet IP2 may be represented by Formula (15) shown below. Furthermore, the mean attenuation coefficient of the bone with respect to the second stimulable phosphor sheet IP2 may be represented by Formula (16) shown below.

$$\overline{\mu_S}' = \frac{\int \mu_S(E)I2(E)dE}{\int I2(E)dE} \quad (15)$$

$$= \frac{\int \mu_S(E)B(E)\exp[-\mu_S(E)t_S - \mu_B(E)t_B]dE}{\int B(E)\exp[-\mu_S(E)t_S - \mu_B(E)t_B]dE}$$

$$\overline{\mu_B}' = \frac{\int \mu_B(E)I2(E)dE}{\int I2(E)dE} \quad (16)$$

$$= \frac{\int \mu_B(E)B(E)\exp[-\mu_S(E)t_S - \mu_B(E)t_B]dE}{\int B(E)\exp[-\mu_S(E)t_S - \mu_B(E)t_B]dE}$$

In cases where the relationship represented by Formula (7) shown above is obtained, from Formula (11) and Formula (12) shown above, the difference between a logarithmic value ln(I1) of the radiation dose I1 and a logarithmic value ln(I2) of the radiation dose I2 may be represented by Formula (17) shown below. (The logarithmic value of the radiation dose will hereinbelow be referred to as the logarithmic radiation dose.)

$$\ln(I1) - \ln(I2) = \ln \frac{\int A(E)\exp[-\mu_S(E)t_S - \mu_B(E)t_B]dE}{\int B(E)\exp[-\mu_S(E)t_S - \mu_B(E)t_B]dE} = \quad (17)$$

$$\ln \frac{\int A(E)\exp\{-\mu_S(E)t_S + [\rho\mu_B(E) + q]t_S\}}{\int B(E)\exp\{-\mu_S(E)t_S + [\rho\mu_B(E) + q]t_S\}} \approx \frac{\exp\{-[\rho\mu_B(E) + q]t_S - \mu_B(E)t_B\}dE}{\exp\{-[\rho\mu_B(E) + q]t_S - \mu_B(E)t_B\}dE}$$

$$\ln \frac{\int A(E)\exp[-\mu_B(E)(pt_S + t_B) - qt_S]dE}{\int B(E)\exp[-\mu_B(E)(pt_S + t_B) - qt_S]dE} =$$

$$\ln \frac{\int A(E)\exp[-\mu_B(E)(pt_S + t_B)]dE}{\int B(E)\exp[-\mu_B(E)(pt_S + t_B)]dE}$$

From Formula (17), it can be found that, in cases where the difference ln(I1)−ln(I2) between the logarithmic radiation doses ln(I1) and ln(I2), is calculated, the logarithmic radiation doses ln(I1) and ln(I2), each of which was expressed with two variables of $t_S$ and $t_B$, are capable of being expressed with one variable of $pt_S+t_B$. As an aid in facilitating the explanation, replacement may be made such that $t=pt_S+t_B$. In such cases, Formula (17) is capable of being rewritten as Formula (18) shown below.

$$\ln(I1) - \ln(I2) = \ln \frac{\int A(E)\exp[-\mu_B(E)t]dE}{\int B(E)\exp[-\mu_B(E)t]dE} \quad (18)$$

As for the mean attenuation coefficients with respect to the first stimulable phosphor sheet IP1, in cases where the relationship represented by Formula (7) is applied to Formula (13) and Formula (14) shown above, and the expressions are arranged, Formula (13) and Formula (14) are capable of being rewritten respectively as Formula (19) and Formula (20).

$$\overline{\mu_S} = \frac{\int \mu_S(E)A(E)\exp[-\mu_S(E)t]dE}{\int A(E)\exp[-\mu_S(E)t]dE} \quad (19)$$

$$\overline{\mu_B} = \frac{\int \mu_B(E)A(E)\exp[-\mu_B(E)t]dE}{\int A(E)\exp[-\mu_B(E)t]dE} \quad (20)$$

Also, as for the mean attenuation coefficients with respect to the second stimulable phosphor sheet IP2, in cases where the relationship represented by Formula (7) is applied to Formula (15) and Formula (16) shown above, and the expressions are arranged, Formula (15) and Formula (16) are capable of being rewritten respectively as Formula (21) and Formula (22).

$$\overline{\mu_S}' = \frac{\int \mu_S(E)B(E)\exp[-\mu_S(E)t]dE}{\int B(E)\exp[-\mu_S(E)t]dE} \quad (21)$$

$$\overline{\mu_B}' = \frac{\int \mu_B(E)B(E)\exp[-\mu_B(E)t]dE}{\int B(E)\exp[-\mu_B(E)t]dE} \quad (22)$$

When the thickness of the substance becomes large, the difference between :the radiation dose I1 of the radiation impinging upon the first stimulable phosphor sheet IP1 and the radiation dose I2 of the radiation impinging upon the second stimulable phosphor sheet IP2 becomes small. Therefore, it may be assumed that Formula (18) shown above is a monotonously decreasing function with respect to "t." Also, in cases where the mean attenuation coefficient decreases monotonously with respect to the radiation energy as illustrated in FIG. 3A, if the thickness of the substance becomes large, and the radiation after passing through,:the substance is biased to the high energy level side, the mean attenuation coefficient will decrease. Accordingly, it may be assumed that Formula (19), Formula (20), Formula (21), and Formula (22) shown above are monotonously decreasing functions with respect to "t." Values of functions, which undergo a monotonous decrease through the intermediary of a certain variable, have a one-to-one correspondence relationship. Therefore, the values of the function of Formula (18) and the function of each of Formula (19), Formula (20), Formula (21), and Formula (22), which functions undergo the monotonous decrease through the intermediary of the variable "t," have the one-to-one correspondence relationship. Accordingly, as represented by each of Formula (23), Formula (24), Formula (25), and Formula (26) shown below, the relationship through each of certain functions $F_S$, $F_B$, $F_S'$, and $F_B'$ is obtained between the logarithmic radiation dose difference and the mean attenuation coefficient.

$$\overline{\mu_S} = F_S[\ln(I1) - \ln(I2)] \tag{23}$$

$$\overline{\mu_B} = F_B[\ln(I1) - \ln(I2)] \tag{24}$$

$$\overline{\mu_S}' = F_S'[\ln(I1) - \ln(I2)] \tag{25}$$

$$\overline{\mu_B}' = F_B'[\ln(I1) - \ln(I2)] \tag{26}$$

Figure 4A:
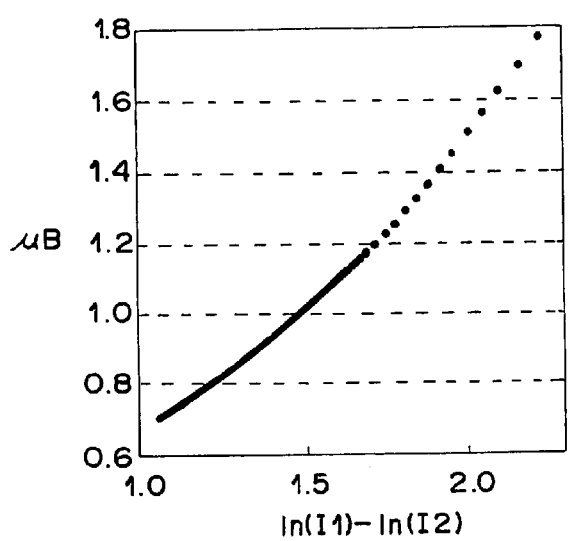
FIG. 4A is a graph showing a relationship between a logarithmic radiation dose difference and the mean attenuation coefficient of the bone, which relationship is obtained when a thickness of the bone is set at various different values.
Figure 4B:
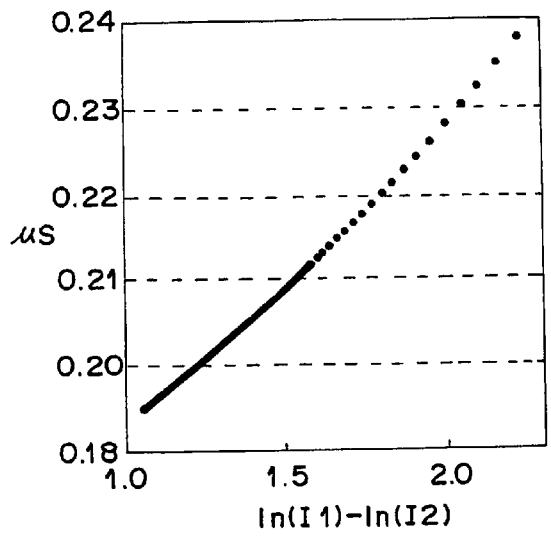
FIG. 4B is a graph showing a relationship between the logarithmic radiation dose difference and the mean attenuation coefficient of the soft tissue, which relationship is obtained when a thickness of the soft tissue is set at various different values.

Therefore, in cases where each of the functions $F_S$, $F_B$, $F_S'$, and $F_B'$ is determined previously through experiments, the mean attenuation coefficient is capable of being calculated from the logarithmic radiation dose difference. FIG. 4A is a graph showing a relationship between the logarithmic radiation dose difference (between the first stimulable phosphor sheet IP1 and the second stimulable phosphor sheet IP2) and the mean attenuation coefficient of the bone with respect to the first stimulable phosphor sheet IP1, which relationship has been obtained experimentally when the thickness of the bone was set at various different values. FIG. 4B is a graph showing a relationship between the logarithmic radiation dose difference (between the first stimulable phosphor sheet IP1 and the second stimulable phosphor sheet IP2) and the mean attenuation coefficient of the soft tissue with respect to the first stimulable phosphor sheet IP1, which relationship has been obtained experimentally when the thickness of the soft tissue was set at various different values. From FIG. 4A and FIG. 4B, it can be found that the logarithmic radiation dose difference and the mean attenuation coefficient have the curvilinear relationship with each other, which may be represented by a certain function.

In this embodiment, (four kinds of) the relationships between the logarithmic radiation dose differences and the mean attenuation coefficients (i.e., the mean attenuation coefficient of the soft tissue with respect to the first stimulable phosphor sheet IP1, the mean attenuation coefficient of the bone with respect to the first stimulable phosphor sheet IP1, the mean attenuation coefficient of the soft tissue with respect to the second stimulable phosphor sheet IP2, and the mean attenuation coefficient of the bone with respect to the second stimulable phosphor sheet IP2), which relationships are represented by the functions $F_S$, $F_B$, $F_S'$ and $F_B'$, are determined previously as the table T. The information representing the table T is stored in the storage means 20. Also, reference is made to the table T, and the mean attenuation coefficients, i.e. the weight factors, which are to be utilized in the subtraction processing means 18 for calculating the difference signal $S_S$ and the difference signal $S_B$ respectively with Formula (5) and Formula (6), are set by the setting means 19.

It is not always possible to directly detect the radiation dose with respect to each of the pixel positions on each of the first stimulable phosphor sheet IP1 and the second stimulable phosphor sheet IP2. However, when the dose of radiation impinging upon each of the first stimulable phosphor sheet IP1 and the second stimulable phosphor sheet IP2 is large, each of the image signal S1 and the image signal S2, which are obtained respectively from the first stimulable phosphor sheet IP1 and the second stimulable phosphor sheet IP2, takes a large signal value. Thus the signal value of the image signal S1 has the correspondence relationship with the radiation dose I1. Also, the signal value of the image signal S2 has the correspondence relationship with the radiation dose I2. Therefore, in this embodiment, the image signal S1 and the image signal S2, which have been obtained from the logarithmic conversion and the analog-to-digital conversion, are utilized respectively as the radiation dose I1 and the radiation dose I2. In such cases, since the image signal S1 and the image signal S2 have already been subjected to the logarithmic conversion, the difference signal between the image signal S1 and the image signal S2 corresponds to the logarithmic radiation dose difference ln(I1)−ln(I2). Therefore, in the storage means 20, the table T is stored as the table representing the relationships between the difference signals S1−S2 and the mean attenuation coefficients.

Figure 5:
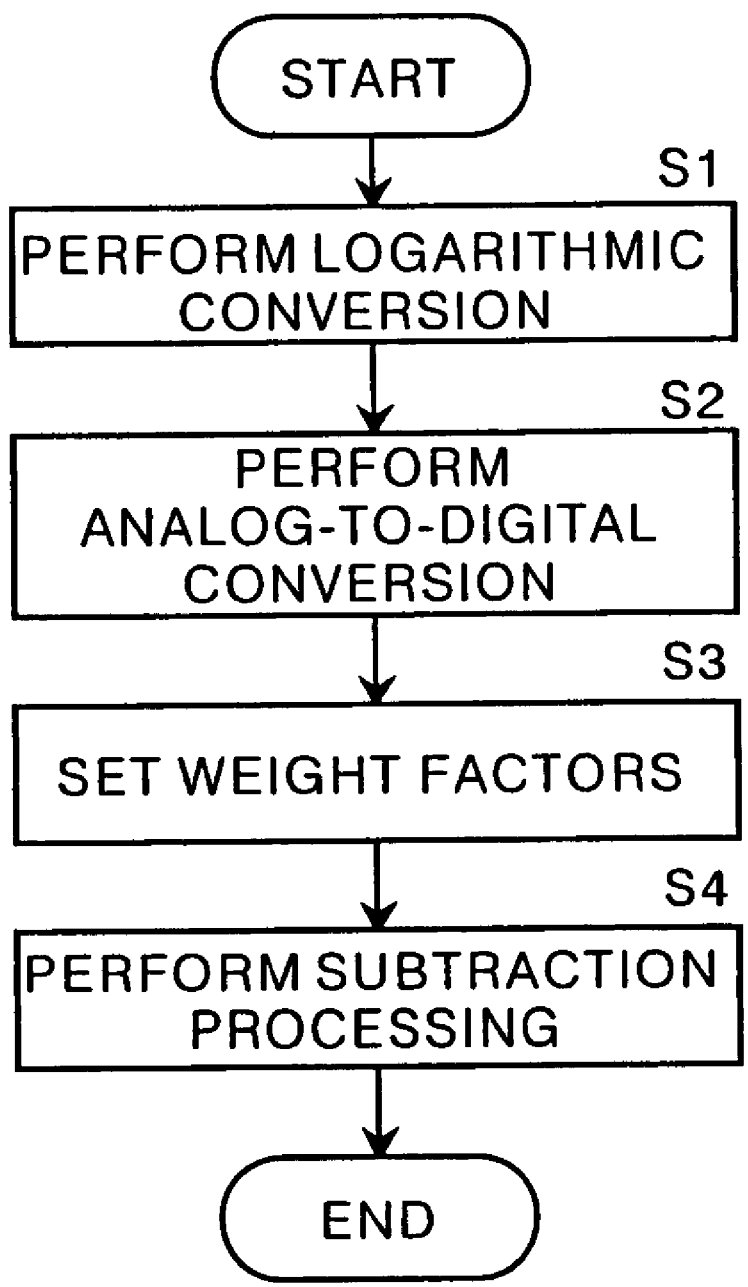
FIG. 5 is a flow chart showing how the first embodiment of the energy subtraction processing apparatus in accordance with the present invention operates.

How the first embodiment of the energy subtraction processing apparatus in accordance with the present invention operates will be described hereinbelow. FIG. 5 is a flow chart showing how the first embodiment of the energy subtraction processing apparatus in accordance with the present invention operates. With reference to FIG. 5, in a step S1, the output signal Q1 having been detected from the first stimulable phosphor sheet IP1 and the output signal Q2 having been detected from the second stimulable phosphor sheet IP2 are subjected to the logarithmic conversion performed by the logarithmic converter 16. In a step S2, the output signal Q1 and the output signal Q2, which have been obtained from the logarithmic conversion, are subjected to the analog-to-digital conversion performed by the analog-to-digital converter 17. The digital image signal S1 and the digital image signal S2 are obtained from the analog-to-digital conversion. The digital image signal S1 and the digital image signal S2 are fed into the setting means 19. In a step S3, in the setting means 19, the difference signal S1−S2, which corresponds to the logarithmic radiation dose difference ln(I1)−ln(I2), is calculated with respect to the corresponding pixels in the radiation images represented by the image signal S1 and the image signal S2. Also, reference is made to the table T in accordance with the difference signal S1−S2, and the mean attenuation coefficients of the soft tissue and the bone with respect to the first stimulable phosphor sheet IP1 and the mean attenuation coefficients of the soft tissue and the bone with respect to the second stimulable phosphor sheet IP2 are set as the weight factors and with respect each of the pixels in the radiation images. The information representing the weight factors is fed into the subtraction processing means 18. In a step S4, in the subtraction processing means 18, the energy subtraction processing is performed, wherein the image signal S1 and the image signal S2 are weighted with the weight factors, and the operation processing represented by Formula (5) shown above and the operation processing represented by Formula (6) shown above are performed. From the energy subtraction processing, the difference signal $S_S$ representing the soft tissue image, in which only the pattern of the soft tissue contained in the object 1 is illustrated, and the difference signal $S_B$ representing the bone: image, in which only the pattern of the bone contained in the object 1 is illustrated, are obtained. In this stage, the processing with the first embodiment of the energy subtraction processing apparatus in accordance with the present invention is finished. The thus obtained difference signal $S_S$ and the thus obtained difference signal $S_B$ are fed into reproducing means (not shown), such as a printer or a CRT display device, and utilized for reproducing visible images to be utilized in making a diagnosis.

As described above, the first embodiment of the energy subtraction processing apparatus in accordance with the present invention is based on the findings that the certain relationship is obtained between the difference between the logarithmic values of the radiation doses with respect to the first stimulable phosphor sheet IP1 and the second stimulable phosphor sheet IP2, i.e. the logarithmic radiation dose difference between the first stimulable phosphor sheet IP1 and the second stimulable phosphor sheet IP2, and the mean attenuation coefficient. With the first embodiment, on the basis of the findings described above, the mean attenuation coefficient, i.e. the weight factor to be utilized in the energy subtraction processing, is set with respect to each of the pixels in each of the radiation images and in accordance with the logarithmic radiation dose difference. The radiation dose with respect to each of the pixels in each of the radiation images varies in accordance with the thickness of the specific structure (i.e., each of the soft tissue and the bone) contained in the object 1. Therefore, the mean attenuation coefficient, which has been set with respect to each of the pixels in each of the radiation images and in accordance with the difference between the logarithmic values of the radiation doses with respect to the corresponding pixels in the radiation images, takes a value in accordance with the thickness of each of the soft tissue and the bone. Accordingly, in cases where the energy subtraction processing, in which the mean attenuation coefficients having been set are utilized as the weight factors for the image signal S1 and the image signal S2, is performed, the difference signal $S_S$ representing the soft tissue image, in which only the pattern of the soft tissue contained in the object 1 is illustrated accurately, and the difference signal $S_B$ representing the bone image, in which only the pattern of the bone contained in the object 1 is illustrated accurately, are capable of being obtained regardless of the thicknesses of the soft tissue and the bone contained in the object 1.

Also, in the first embodiment described above, the table T, which represents the relationships between the logarithmic radiation dose differences and the mean attenuation coefficients, is determined previously. Therefore, the weight factors are capable of being set easily. Accordingly, the calculation of the difference signal $S_S$ and the calculation of the difference signal $S_B$ are capable of being made efficiently.

In the first embodiment described above, each of the mean attenuation coefficients is set in accordance with the logarithmic radiation dose difference ln(I1)−ln(I2) between the radiation dose I1 and the radiation dose I2. Alternatively, since the relationship represented by the formula ln(I1)−ln(I2)=ln(I1/I2) is obtained, each of the mean attenuation coefficients may be set in accordance with the logarithmic value ln(I1/I2) of the ratio I1/I2 between the radiation dose I1 and the radiation dose I2.

Also, in the first embodiment described above, the relationships between the logarithmic radiation dose differences and the mean attenuation coefficients are determined as the table T. Alternatively, the information representing the functions $F_S$, $F_B$, $F_S'$, and $F_B'$ may be stored in the storage means 20, and the mean attenuation coefficient may be calculated from the logarithmic radiation dose difference ln(I1)−ln(I2) by the utilization of each of the functions $F_S$, $F_B$, $F_S'$, and $F_B'$.

Figure 6:
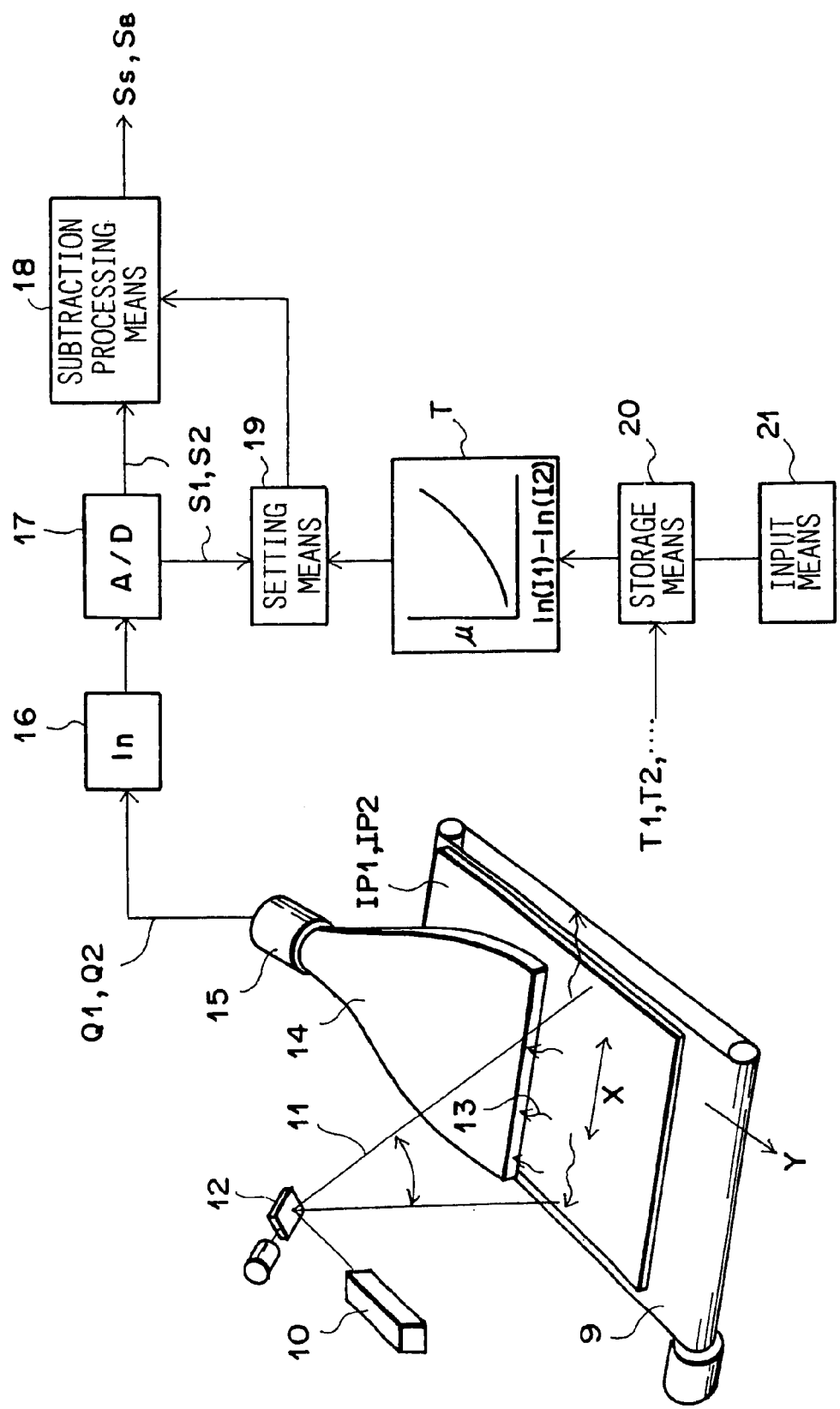
FIG. 6 is a perspective view showing a radiation image read-out apparatus, in which a second embodiment of the energy subtraction processing apparatus in accordance with the present invention is employed.

The relationship between the logarithmic radiation dose difference and the mean attenuation coefficient varies for different image recording conditions employed in the image recording operation, such as the voltage of the radiation source 3, the kind of the radiation source 3, and the sensitivities of the first stimulable phosphor sheet IP1 and the second stimulable phosphor sheet IP2. Therefore, as in a second embodiment of the energy subtraction processing apparatus in accordance with the present invention, which second embodiment is illustrated in FIG. 6, a plurality of tables T1, T2, . . . in accordance with various different image recording conditions may be prepared previously, and the information representing the plurality of the tables T1, T2, . . . may be stored in the storage means 20. Also, the image recording conditions employed in the image recording operation may be inputted from input means 21, which may be constituted of a keyboard, a mouse device, or the like. Further, a table T appropriate for the image recording conditions may be selected in accordance with the inputted image recording conditions, and the mean attenuation coefficient may be set by the utilization of the selected table T.

Further, in the first and second embodiments described above, the first stimulable phosphor sheet IP1 and the second stimulable phosphor sheet IP2 are employed as the radiation detecting means, and the image signal S1 and the image signal S2 are obtained from the first stimulable phosphor sheet IP1 and the second stimulable phosphor sheet IP2. Alternatively, other kinds of radiation detecting means, such as X-ray film and semiconductor sensors, may be employed.

Furthermore, in the first and second embodiments described above, the one-shot energy subtraction processing technique, wherein the two radiation images to be subjected to the energy subtraction processing are formed simultaneously with one image recording operation, is employed. However, the energy subtraction processing apparatus in accordance with the present invention is not limited to the utilization of the one-shot energy subtraction processing technique. The energy subtraction processing apparatus in accordance with the present invention is also applicable to the cases where a multi-shot energy subtraction processing technique, in which at least two kinds of radiation having different energy distributions are irradiated one after the other to the object, and the radiation images are formed on at least two stimulable phosphor sheets one after the other with at least two image recording operations, is employed, and the image signals obtained with the multi-shot energy subtraction processing technique are subjected to the energy subtraction processing. In cases where the multi-shot energy subtraction processing technique is employed, a plurality of image signals are obtained. Of the plurality of the image signals, two image signals are selected and subjected to the energy subtraction processing.

Figure 7:
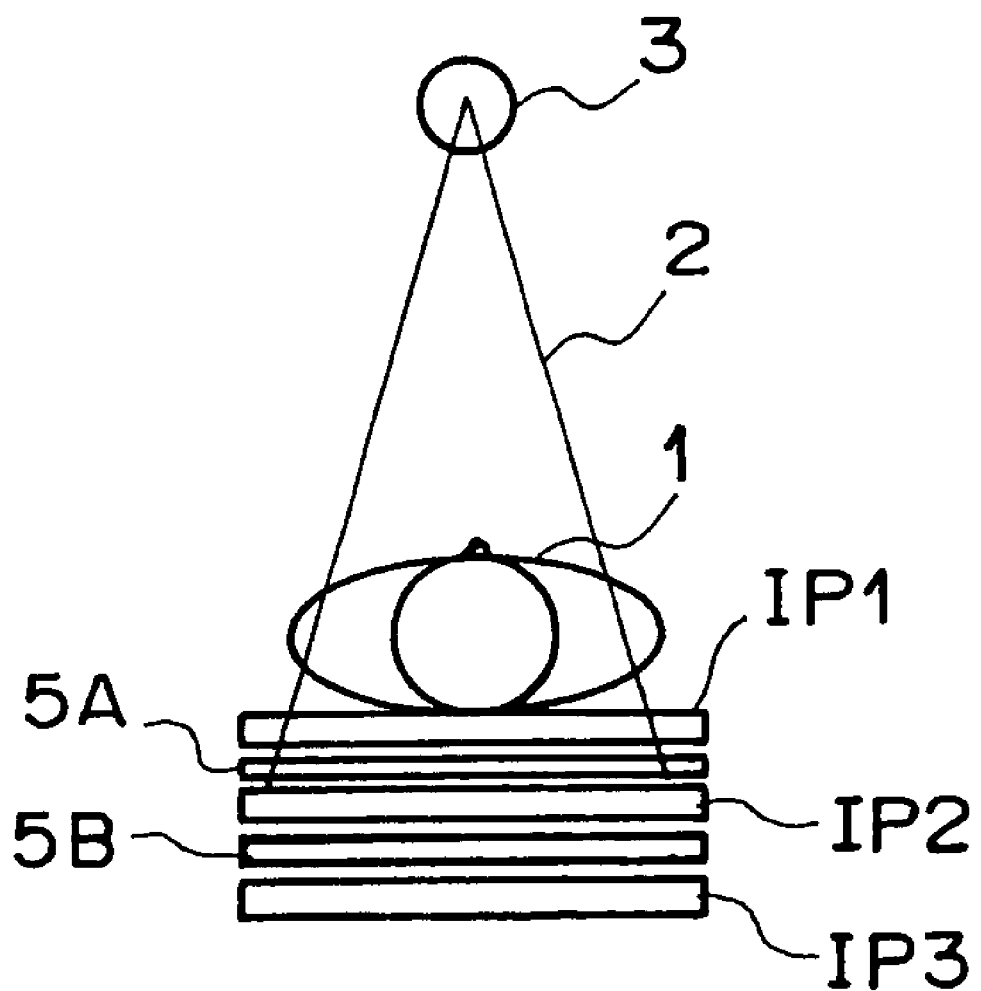
FIG. 7 is a schematic view showing a different example of how radiation images are recorded on stimulable phosphor sheets.

FIG. 7 shows a different example of a radiation image recording apparatus for performing the one-shot energy subtraction processing technique, in which the radiation 2 carrying the image information of the object 1 is irradiated simultaneously to the first stimulable phosphor sheet IP1, the second stimulable phosphor sheet IP2, and a third stimulable phosphor sheet IP3 such that the three stimulable phosphor sheets IP1, IP2, and IP3 are exposed respectively to three kinds of radiation having different energy distributions. As illustrated in FIG. 7, the first, stimulable phosphor sheet IP1 is located at a position close to the radiation source 3 for producing the radiation 2, and the second stimulable phosphor sheet IP2 is located at a position remote from the radiation source 3 and with a slight spacing from the first stimulable phosphor sheet IP1. Also, the third stimulable phosphor sheet IP3 is located at a position, which is remoter from the radiation source 3 than the second stimulable phosphor sheet IP2 is, and with a slight spacing from the second stimulable phosphor sheet IP2. Further, a radiation energy converting filter 5A, which may be constituted of a copperplate, is located between the first stimulable phosphor sheet IP1 and the second stimulable phosphor sheet IP2, and a radiation energy converting filter 5B, which may be constituted of a copper plate, is located between the second stimulable phosphor sheet IP2 and the third stimulable phosphor sheet IP3. In this state, the radiation source 3 is driven. As a result, a radiation image of the object 1 is formed on the first stimulable phosphor sheet IP1 and with the radiation 2 having a low energy level and containing the so-called "soft rays." Also, a radiation image of the object 1 is formed on the second stimulable phosphor sheet IP2 and with the radiation 2, which has a medium energy level and from which the soft rays have been removed. Further, a radiation image of the object 1 is formed on the third stimulable phosphor sheet IP3 and with the radiation 2, which has a high energy level and from which the soft rays have been removed even further. At this time, the relationship between the position of the object 1 and the position of the first stimulable phosphor sheet IP1, the relationship between the position of the object 1 and the position of the second stimulable phosphor sheet IP2, and the relationship between the position of the object 1 and the position of the third stimulable phosphor sheet IP3 are identical with one another. In this manner, three radiation images, in which different images of at least part of the object 1 are embedded, are stored respectively on the three stimulable phosphor sheets IP1, IP2, and IP3.

FIG. 8 is a perspective view showing a radiation image read-out apparatus, in which a third embodiment of the energy subtraction processing apparatus in accordance with the present invention is employed. With reference to FIG. 8, of the three stimulable phosphor sheets IP1, IP2, and IP3, on which the radiation images of the object 1 have been stored, the first stimulable phosphor sheet IP1 is firstly set on the endless belt 9. The first stimulable phosphor sheet IP1 is moved by the endless belt 9 in the sub-scanning direction indicated by the arrow Y. At the same time, the laser beam 11, which serves as stimulating rays, is produced by the laser beam source 10. The laser beam 11 is deflected by the scanning mirror 12 and caused to scan the first stimulable phosphor sheet IP1 in the main scanning directions indicated by the double-headed arrow X. When the first stimulable phosphor sheet IP1 is exposed to the laser beam 11, the first stimulable phosphor sheet IP1 emits the light 13 in proportion to the amount of energy stored thereon during its exposure to the radiation 2. The emitted light 13 enters into the light guide member 14, which is made from a transparent acrylic plate, from one end face of the light guide member 14. The emitted light 13 is guided through repeated total reflection inside of the light guide member 14 and detected by the photomultiplier 15. The photomultiplier 15 generates the analog output signal Q1 corresponding to the intensity of the emitted light 13, i.e. representing the radiation image having been stored on the first stimulable phosphor sheet IP1.

The output signal Q1 is logarithmically converted by the logarithmic converter 16 and is then converted by the analog-to-digital converter 17 into the digital image signal S1. Thereafter, the radiation image having been stored on the second stimulable phosphor sheet IP2 is read out in the same manner as that described above, and the output signal Q2 representing the radiation image is thereby obtained. The output signal Q2 is logarithmically converted by the logarithmic converter 16 and is then converted by the analog-to-digital converter 17 into the digital image signal S2. Also, the radiation image having been stored on the third stimulable phosphor sheet IP3 is read out in the same manner as that described above, and an output signal Q3 representing the radiation image is thereby obtained. The output signal Q3 is logarithmically converted by the logarithmic converter 16 and is then converted by the analog-to-digital converter 17 into a digital image signal S3.

The image signal S1, the image signal S2, and the image signal S3 are fed into subtraction processing means 118. In the subtraction processing means 118, energy subtraction processing is performed on the received image signals. From the energy subtraction processing, the difference signal $S_S$ representing the soft tissue image, in which only the pattern of the soft tissue contained in the object 1 is illustrated, and the difference signal $S_B$ representing the bone image, in which only the pattern of the bone contained in the object 1 is illustrated, are obtained. Weight factors for the image signals S1, S2, and S3, which weight factors are to be utilized for the energy subtraction processing, are set by setting means 119. The setting means 119 makes reference to a table T' having been stored in the storage means 20 and sets the weight factors. How the weight factors are set will be described hereinbelow.

FIG. 9 is an explanatory view showing how the setting means 119 is constituted and how processing in the setting means 119 is performed. As illustrated in FIG. 9, the setting means 119 comprises mean attenuation coefficient calculating means 119A and weighted mean value calculating means 119B. The mean attenuation coefficient calculating means 119A calculates the mean attenuation coefficients in the manner described later. The weighted mean value calculating means 119B calculates weighted mean values of the mean attenuation coefficients, which have been calculated by the mean attenuation coefficient calculating means 119A, in order to calculate the weight factors for use in the energy subtraction processing performed by the subtraction processing means 118.

In the subtraction processing means 118, the energy subtraction processing is performed on a combination of the image signal S1 and the image signal S2, a combination of the image signal S1 and the image signal S3, or a combination of the image signal S2 and the image signal S3. By way of example, in cases where the energy subtraction processing is to be performed on the combination of the image signal S1 and the image signal S2, in the same manner as that in the first embodiment described above, the energy subtraction processing is performed with Formula (5) shown below, and the difference signal $S_S$ representing the soft tissue image, in which only the pattern of the soft tissue contained in the object 1 is illustrated, is obtained. Also, the energy subtraction processing is performed with Formula (6) shown below, and the difference signal $S_B$ representing the bone image, in which only the pattern of the bone contained in the object 1 is illustrated, is obtained.

$$S_S = \overline{\mu_B}' S2 - \overline{\mu_B} S1 = (\overline{\mu_S} \overline{\mu_B}' - \overline{\mu_S}' \overline{\mu_B}) t_S + (\overline{\mu_B}' I2_0 - \overline{\mu_B}' I1_0) \quad (5)$$

$$S_B = \overline{\mu_S} S2 - \overline{\mu_S}' S1 = (\overline{\mu_S}' \overline{\mu_B} - \overline{\mu_{SB}}') t_B + (\overline{\mu_S} I2_0 - \overline{\mu_S}' I1_0) \quad (6)$$

wherein
- $\overline{\mu_B}$ represents the mean attenuation coefficient of the bone with respect to the first stimulable phosphor sheet IP1,
- $\overline{\mu_S}$ represents the mean attenuation coefficient of the soft tissue with respect to the first stimulable phosphor sheet IP1,
- $\overline{\mu_B}'$ represents the mean attenuation coefficient of the bone with respect to the second stimulable phosphor sheet IP2,
- $\overline{\mu_S}'$ represents the mean attenuation coefficient of the soft tissue with respect to the second stimulable phosphor sheet IP2,
- $t_S$ represents the thickness of the bone,
- $t_B$ represents the thickness of the soft tissue, and
- each of $I1_0$ and $I2_0$ represents the fixed number depending upon the radiation source.

In Formula (5) and Formula (6), the mean attenuation coefficients, by which the image signals S1 and S2 are multiplied, act as the weight factors.

A substance has a radiation attenuation coefficient depending upon radiation energy. Also, in cases where the radiation irradiated to the object is not monochromatic and is distributed over a certain energy range, the energy distribution of the radiation impinging upon each of the first stimulable phosphor sheet IP1, the second stimulable phosphor sheet IP2, and the third stimulable phosphor sheet IP3 changes depending upon the thickness of a substance (i.e., the bone or the soft tissue) contained in the object. Such a phenomenon is referred to as the beam hardening. Therefore, in the third embodiment, the radiation attenuation coefficient of the substance is weighted with the energy distribution of the detected radiation (i.e., the radiation having impinged upon the stimulable phosphor sheet) and averaged. The thus obtained value is defined as the mean attenuation coefficient. Accordingly, the mean attenuation coefficient varies for different thicknesses of the substance.

As described above with reference to Formulas (7) through Formula (22), in cases where it is assumed that only the first stimulable phosphor sheet IP1 and the second stimulable phosphor sheet IP2 are utilized, the relationship through each of the certain functions $F_S$, $F_B$, $F_S'$, and $F_B'$ is obtained between the logarithmic radiation dose difference and the mean attenuation coefficient. The relationship is represented by each of Formula (23), Formula (24), Formula (25), and Formula (26) shown below. (In this case, $t_{cu}$ in Formula (10) shown above represents the thickness of the radiation energy converting filter 5A.)

$$\overline{\mu}_S = F_S[\ln(I1) - \ln(I2)] \tag{23}$$

$$\overline{\mu}_B = F_B[\ln(I1) - \ln(I2)] \tag{24}$$

$$\overline{\mu}_S' = F_S'[\ln(I1) - \ln(I2)] \tag{25}$$

$$\overline{\mu}_B' = F_B'[\ln(I1) - \ln(I2)] \tag{26}$$

Therefore, in cases where each of the functions $F_S$, $F_B$, $F_S'$, and $F_B'$ is determined previously through experiments, the mean attenuation coefficient is capable of being calculated from the logarithmic radiation dose difference. FIG. 4A shows the relationship between the logarithmic radiation dose difference (between the first stimulable phosphor sheet IP1 and the second stimulable phosphor sheet IP2) and the mean attenuation coefficient of the bone with respect to the first stimulable phosphor sheet IP1, which relationship has been obtained experimentally when the thickness of the bone was set at various different values. FIG. 4B shows the relationship between the logarithmic radiation dose difference (between the first stimulable phosphor sheet IP1 and the second stimulable phosphor sheet IP2) and the mean attenuation coefficient of the soft tissue with respect to the first stimulable phosphor sheet IP1, which relationship has been obtained experimentally when the thickness of the soft tissue was set at various different values. From FIG. 4A and FIG. 4B, it can be found that the logarithmic radiation dose difference and the mean attenuation coefficient have the curvilinear relationship with each other, which may be represented by a certain function.

The mean attenuation coefficient of the bone and the mean attenuation coefficient of the soft tissue are calculated with respect to each of the first stimulable phosphor sheet IP1, the second stimulable phosphor sheet IP2, and the third stimulable phosphor sheet IP3. As an aid in facilitating the explanation, the mean attenuation coefficient (of each of the bone and the soft tissue) with respect to the first stimulable phosphor sheet IP1 may be represented by $\mu(IP1)$. Also, the mean attenuation coefficient (of each of the bone and the soft tissue) with respect to the second stimulable phosphor sheet IP2 may be represented by $\mu(IP2)$. Further, the mean attenuation coefficient (of each of the bone and the soft tissue) with respect to the third stimulable phosphor sheet IP3 may be represented by $\mu(IP3)$ In such cases, as described above, the mean attenuation coefficients $\mu(IP1)$ and $\mu(IP2)$ are capable of being calculated from the logarithmic radiation dose difference between the first stimulable phosphor sheet IP1 and the second stimulable phosphor sheet IP2. Also, the mean attenuation coefficients $\mu(IP1)$ and $\mu(IP3)$ are capable of being calculated from the logarithmic radiation dose difference between the first stimulable phosphor sheet IP1 and the third stimulable phosphor sheet IP3. Further, the mean attenuation coefficients $\mu(IP2)$ and $\mu(IP3)$ are capable of being calculated from the logarithmic radiation dose difference between the second stimulable phosphor sheet IP2 and the third stimulable phosphor sheet IP3. Therefore, the mean attenuation coefficient $\mu(IP1)$ with respect to the first stimulable phosphor sheet IP1 is capable of being calculated from the logarithmic radiation dose difference between the first stimulable phosphor sheet IP1 and the second stimulable phosphor sheet IP2, and from the logarithmic radiation dose difference between the first stimulable phosphor sheet IP1 and the third stimulable phosphor sheet IP3. Also, the mean attenuation coefficient $\mu(IP2)$ with respect to the second stimulable phosphor sheet IP2 is capable of being calculated from the logarithmic radiation dose difference between the first stimulable phosphor sheet IP1 and the second stimulable phosphor sheet IP2, and from the logarithmic radiation dose difference between the second stimulable phosphor sheet IP2 and the third stimulable phosphor sheet IP3. Further, the mean attenuation coefficient $\mu(IP3)$ with respect to the third stimulable phosphor sheet IP3 is capable of being calculated from the logarithmic radiation dose difference between the first stimulable phosphor sheet IP1 and the third stimulable phosphor sheet IP3, and from the logarithmic radiation dose difference between the second stimulable phosphor sheet IP2 and the third stimulable phosphor sheet IP3.

It is herein assumed that the relationship represented by Formula (27) shown below is obtained between the mean attenuation coefficient $\mu(IP1)$ with respect to the first stimulable phosphor sheet IP1 and the logarithmic radiation dose difference between the first stimulable phosphor sheet IP1 and the second stimulable phosphor sheet IP2. Also, it is herein assumed that the relationship represented by Formula (28) shown below is obtained between the mean attenuation coefficient $\mu(IP1)$ with respect to the first stimulable phosphor sheet IP1 and the logarithmic radiation dose difference between the first stimulable phosphor sheet IP1 and the third stimulable phosphor sheet IP3.

$$\mu(IP1) = F[\ln(I1) - \ln(I2)] \tag{27}$$

$$\mu(IP1) = G[\ln(I1) - \ln(I3)] \tag{28}$$

wherein

I3 represents the dose of the radiation impinging upon the third stimulable phosphor sheet IP3, F represents the function representing the relationship between the logarithmic radiation dose difference $\ln(I1) - \ln(I2)$ and the mean attenuation coefficient $\mu(IP1)$, and G represents the function representing the relationship between the logarithmic radiation dose difference $\ln(I1) - \ln(I3)$ and the mean attenuation coefficient $\mu(IP1)$.

In cases where Formula (27) is solved for the logarithmic radiation dose difference ln(I1)−ln(I2), Formula (29) shown below is obtained. Also, in cases where Formula (28) is solved for the logarithmic radiation dose difference ln(I1)−ln(I3), Formula (30) shown below is obtained.

$$\ln(I1)-\ln(I2) = F^{-1}[\mu(IP1)] \tag{29}$$

$$\ln(I1)-\ln(I3) = G^{-1}[\mu(IP1)] \tag{30}$$

wherein $F^{-1}$ represents the inverse function of F, and $G^{-1}$ represents the inverse function of G.

A calculation of the difference between Formula (29) and Formula (30), i.e. −Formula (29)+Formula (30), yields Formula (31) shown below.

$$\begin{aligned}-\{\ln(I1)-\ln(I2)\}+\{\ln(I1)-\ln(I3)\} &= \ln(I2)-\ln(I3) \\ &= -F^{-1}[\mu(IP1)] + G^{-1}[\mu(IP1)] \\ &= (-F^{-1}+G^{-1})[\mu(IP1)]\end{aligned} \tag{31}$$

In Formula (31), the part $-F^{-1}+G^{-1}$ is the function. When the inverse function $(-F^{-1}+G^{-1})^{-1}$ of the function $(-F^{-1}+G^{-1})$ is utilized, Formula (32) shown below is obtained.

$$\mu(IP1) = (-F^{-1}+G^{-1})^{-1}[\ln(I2)-(I3)] \tag{32}$$

From Formula (32), it can be found that the mean attenuation coefficient $\mu(IP1)$ with respect to the first stimulable phosphor sheet IP1 is capable of being calculated also from the logarithmic radiation dose difference ln(I2)−ln(I3) between the second stimulable phosphor sheet IP2 and the third stimulable phosphor sheet IP3.

In the same manner as that described above, it can be found that the mean attenuation coefficient $\mu(IP2)$ with respect to the second stimulable phosphor sheet IP2 is capable of being calculated also from the logarithmic radiation dose difference ln(I1)−ln(I3) between the first stimulable phosphor sheet IP1 and the third stimulable phosphor sheet IP3. Further, it can be found that the mean attenuation coefficient (IP3) with respect to the third stimulable phosphor sheet IP3 is capable of being calculated also from the logarithmic radiation dose difference ln(I1)−ln(I2) between the first stimulable phosphor sheet IP1 and the second stimulable phosphor sheet IP2. Therefore, the mean attenuation coefficients $\mu(IP1)$, $\mu(IP2)$, and $\mu(IP3)$ with respect to all of the first stimulable phosphor sheet IP1, the second stimulable phosphor sheet IP2, and the third stimulable phosphor sheet IP3 are capable of being calculated from the logarithmic radiation dose difference, which is calculated for any of combinations of two stimulable phosphor sheets among the first stimulable phosphor sheet IP1, the second stimulable phosphor sheet IP2, and the third stimulable phosphor sheet IP3. FIG. 10 is a graph showing a relationship between the logarithmic radiation dose difference, which is calculated for each of combinations of two stimulable phosphor sheets among the stimulable phosphor sheets IP1, IP2, and IP3, and the mean attenuation coefficient with respect to a certain stimulable phosphor sheet, which relationship has been determined experimentally by the inventors. As illustrated in FIG. 10, it can be found that the mean attenuation coefficient is capable of being calculated from the logarithmic radiation dose difference, which is calculated for any of the combinations of two stimulable phosphor sheets among the first stimulable phosphor sheet IP1, the second stimulable phosphor sheet IP2, and the third stimulable phosphor sheet IP3.

The mean attenuation coefficients with respect to the stimulable phosphor sheets IP1, IP2, and IP3, which mean attenuation coefficients are calculated from the logarithmic radiation dose difference ln(I1)−ln(I2), will hereinbelow be represented respectively by $\mu_1(IP1)$, $\mu_1(IP2)$, and $\mu_1(IP3)$. Also, the mean attenuation coefficients with respect to the stimulable phosphor sheets IP1, IP2, and IP3, which mean attenuation coefficients are calculated from the logarithmic radiation dose difference ln(I1)−ln(I3), will hereinbelow be represented respectively by $\mu_2(IP1)$, $\mu_2(IP2)$, and $\mu_2(IP3)$. Further, the mean attenuation coefficients with respect to the stimulable phosphor sheets IP1, IP2, and IP3, which mean attenuation coefficients are calculated from the logarithmic radiation dose difference ln(I2)−ln(I3), will hereinbelow be represented respectively by $\mu_3(IP1)$, $\mu_3(IP2)$, and $\mu_3(IP3)$.

In the third embodiment, for each of the logarithmic radiation dose differences ln(I1)−ln(I2), ln(I1)−ln(I3), and ln(I2)−ln(I3) among the three stimulable phosphor sheets IP1, IP2, and IP3, the relationship between the logarithmic radiation dose difference and each of mean attenuation coefficients $\mu_k(IP1)$ $\mu_k(IP2)$, and $\mu_k(IP3)$, where k=1 to 3, with respect to all of the stimulable phosphor sheets IP1, IP2, and IP3 is determined previously as the table T'. The information representing the table T' is stored in the storage means 20. Also, reference is made to the table T', and the mean attenuation coefficients $\mu_k(IP1)$ $\mu_k(IP2)$, and $\mu_k(IP3)$, where k=1 to 3, are thereby capable of being determined.

In the third embodiment, the mean attenuation coefficients $\mu_k(IP1)$, $\mu_k(IP2)$, and $\mu_k(IP3)$, where k=1 to 3, are determined for each of the bone and the soft tissue. Therefore, as the table T', 18 kinds [=the number of the combinations for the calculation of the logarithmic radiation dose difference (3)×the number of the stimulable phosphor sheets (3)×the number of the specific structures (2)] of tables are prepared. The information representing the 18 kinds of the tables acting as the table T' is stored in the storage means 20.

Figure 11:
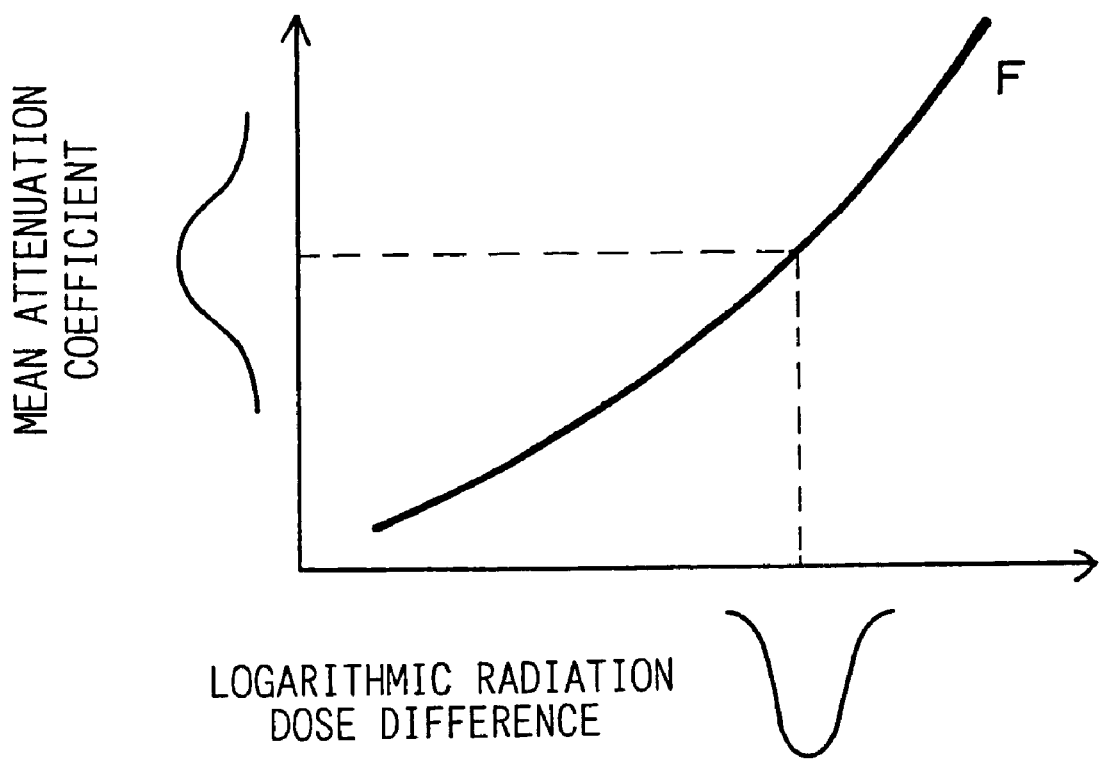
FIG. 11 is a graph showing a relationship between the logarithmic radiation dose difference and the mean attenuation coefficient.

The radiation 2 impinging upon each of the stimulable phosphor sheets IP1, IP2, and IP3 contains quantum noise and scattered radiation, which is scattered when the radiation 2 passes through the object 1. Therefore, it is considered that, due to adverse effects of the quantum noise contained in the radiation 2, the scattered radiation, and the like, the logarithmic radiation dose difference deviates from a true value, i.e. the logarithmic radiation dose difference which will be obtained in cases where the noise, the scattered radiation, and the like, are not contained in the radiation 2. Accordingly, as illustrated in FIG. 11, it is considered that the mean attenuation coefficient deviates from a true value. Also, it is considered that the deviations of the logarithmic radiation dose difference and the mean attenuation coefficient from the true values occur in the normal distribution. As illustrated in FIG. 11, in cases where the relationship between the logarithmic radiation dose difference and the mean attenuation coefficient is represented by a certain function F, the normal distribution of the mean attenuation coefficient changes depending upon the normal distribution of the logarithmic radiation dose difference and the inclination of the function F.

As an aid in facilitating the explanation, replacement may be made with respect to the logarithmic radiation dose differences such that ln(I1)−ln(I2)=Ia, ln(I1)−ln(I3)=Ib, and ln(I2)−ln(I3)=Ic. Also, the mean attenuation coefficients with respect to the first stimulable phosphor sheet IP1, which are calculated from the logarithmic radiation dose differences Ia, Ib, and Ic, may be represented respectively by $\mu_1(IP1)$, $\mu_2(IP1)$ and $\mu_3(IP1)$. Further, the function, which represents the relationship between the logarithmic radiation dose difference Ia and the mean attenuation coefficient $\mu_1(IP1)$, may be represented by $F_{1-1}$. Furthermore, the function, which represents the relationship between the logarithmic radiation dose difference Ib and the mean attenuation coefficient $\mu_2(IP1)$, may be represented by $F_{1-2}$. Also, the function, which represents the relationship between the logarithmic radiation dose difference Ic and the mean attenuation coefficient $\mu_3(IP1)$, may be represented by $F_{1-3}$. Further, standard deviations of the logarithmic radiation dose differences Ia, Ib, and Ic may be represented respectively by σa, σb, and σc. In such cases, a standard deviation $\sigma\mu_1(IP1)$ of the mean attenuation coefficient $\mu_1(IP1)$, which is calculated from the logarithmic radiation dose difference Ia, may be represented by Formula (33) shown below. Also, a standard deviation $\sigma\mu_2(IP1)$ of the mean attenuation coefficient $\mu_2(IP1)$, which is calculated from the logarithmic radiation dose difference Ib, may be represented by Formula (34) shown below. Further, a standard deviation $\mu_3(IP1)$ of the mean attenuation coefficient $\mu_3(IP1)$, which is calculated from the logarithmic radiation dose difference Ic, may be represented by Formula (35) shown below.

$$\sigma\mu_1(IP1) = \frac{dF_{1-1}(Ia)}{dIa}\sigma a \quad (33)$$

$$\sigma\mu_2(IP1) = \frac{dF_{1-2}(Ib)}{dIb}\sigma b \quad (34)$$

$$\sigma\mu_3(IP1) = \frac{dF_{1-3}(Ic)}{dIc}\sigma c \quad (35)$$

A probability $p_{1-1}(\mu_{T1})$ that the calculated mean attenuation coefficient $\mu_1(IP1)$ will be a true mean attenuation coefficient $\mu_T(IP1)$ (hereinbelow referred to simply as $\mu_{T1}$) may be represented by Formula (36) shown below. Also, a probability $p_{1-2}(\mu_{T1})$ that the calculated mean attenuation coefficient $\mu_2(IP1)$ will be the true mean attenuation coefficient IT1 may be represented by Formula (37) shown below. Further, a probability $\mu_{1-3}(\mu_{T1})$ that the calculated mean attenuation coefficient $\mu_3(IP1)$ will be the true mean attenuation coefficient $\mu_{T1}$ may be represented by Formula (38) shown below.

$$p_{1-1}(\mu_{T1}) = \frac{1}{\sqrt{2\pi}\ \sigma a(dF_{1-1}(Ia)/dIa)}\exp\left[-\frac{(\mu_T - \mu_1(IP1))^2}{2\{\sigma a(dF_{1-1}(Ia)/dIa)\}^2}\right] \quad (36)$$

$$p_{1-2}(\mu_{T1}) = \frac{1}{\sqrt{2\pi}\ \sigma b(dF_{1-2}(Ib)/dIb)}\exp\left[-\frac{(\mu_T - \mu_2(IP1))^2}{2\{\sigma b(dF_{1-2}(Ib)/dIb)\}^2}\right] \quad (37)$$

$$p_{1-3}(\mu_{T1}) = \frac{1}{\sqrt{2\pi}\ \sigma c(dF_{1-3}(Ic)/dIc)}\exp\left[-\frac{(\mu_T - \mu_3(IP1))^2}{2\{\sigma c(dF_{1-3}(Ic)/dIc)\}^2}\right] \quad (38)$$

It is herein assumed that the true mean attenuation coefficient $\mu_{T1}$ is calculated as $\mu_{T1}$ obtained in cases where the value of $p_{1-1}(\mu_{T1}) \cdot p_{1-2}(\mu_{T1}) \cdot p_{1-3}(\mu_{T1})$ takes the maximum value. In such cases, the condition required for the value of $p_{1-1}(\mu_{T1}) \cdot p_{1-2}(\mu_{T1}) \cdot p_{1-3}(\mu_{T1})$ to take the maximum value is that, as represented by Formula (39) shown below, the absolute value of the sum of exp[ ] in Formula (36), Formula (37), and Formula (38) becomes minimum.

$$\left| -\frac{(\mu_T - \mu_1(IP1))^2}{2\left\{\sigma a\left(\frac{dF_{1-1}(Ia)}{dIa}\right)\right\}^2} - \frac{(\mu_T - \mu_2(IP1))^2}{2\left\{\sigma b\left(\frac{dF_{1-2}(Ib)}{dIb}\right)\right\}^2} - \frac{(\mu_T - \mu_3(IP1))^2}{2\left\{\sigma c\left(\frac{dF_{1-3}(Ic)}{dIc}\right)\right\}^2} \right| \to \min \quad (39)$$

As an aid in facilitating the explanation, replacement may be made as represented by Formula (40), Formula (41), and Formula (42) shown below.

$$A_{1-1} = \sigma a\left(\frac{F_{1-1}(Ia)}{dIa}\right)^{-2} \quad (40)$$

$$A_{1-2} = \sigma b\left(\frac{F_{1-2}(Ib)}{dIb}\right)^{-2} \quad (41)$$

$$A_{1-3} = \sigma c\left(\frac{F_{1-3}(Ic)}{dIc}\right)^{-2} \quad (42)$$

In such cases, the true mean attenuation coefficient $\mu_{T1}$ may be represented by Formula (43) shown below.

$$\mu_{T1} = \frac{A_{1-1}\mu_1(IP1) + A_{1-2}\mu_2(IP1) + A_{1-3}\mu_3(IP1)}{A_{1-1} + A_{1-2} + A_{1-3}} \quad (43)$$

Therefore, as for the first stimulable phosphor sheet IP1, the mean value of the mean attenuation coefficients $\mu_1(IP)$, $\mu_2(IP1)$, and $\mu_3(IP1)$ may be calculated with the weighted mean calculating process, wherein the mean attenuation coefficients $\mu_1(IP1)$, $\mu_2(IP1)$, and $\mu_3(IP1)$, which have been calculated with respect to the first stimulable phosphor sheet IP1 and respectively from the logarithmic radiation dose differences Ia, Ib, and Ic among the stimulable phosphor sheets IP1, IP2, and IP3, are weighted with the coefficients $A_{1-1}$, $A_{1-2}$, and $A_{1-3}$ calculated in accordance with the standard deviations of the mean attenuation coefficients $\mu_1(IP1)$, $\mu_2(IP1)$, and $\mu_3(IP1)$. In this manner, the mean attenuation coefficient $\mu_{T1}$, which is closest to the true value, is capable of being calculated.

In the same manner, as for the second stimulable phosphor sheet IP2, the mean value of the mean attenuation coefficients $\mu_1(IP2)$ $\mu_2(IP2)$, and $\mu_3(IP2)$ may be calculated with the weighted mean calculating process, wherein the mean attenuation coefficients $\mu_1(IP2)$, $\mu_2(IP2)$, and $\mu_3(IP2)$, which have been calculated with respect to the second stimulable phosphor sheet IP2 and respectively from the logarithmic radiation dose differences Ia, Ib, and Ic among the stimulable phosphor sheets IP1, IP2, and IP3, are weighted with the coefficients (which may be represented by $A_{2-1}$, $A_{2-2}$, and $A_{2-3}$) calculated in accordance with the standard deviations of the mean attenuation coefficients $\mu_1(IP2)$, $\mu_2(IP2)$, and $\mu_3(IP2)$. The weighted mean calculating process is made with Formula (44) shown below. In this manner, the mean attenuation coefficient $\mu_{T2}$, which is closest to the true value, is capable of being calculated. Further, as for the third stimulable phosphor sheet IP3, the mean value of the mean attenuation coefficients $\mu_1(IP3)$, $\mu_2(IP3)$, and $\mu_3(IP3)$ may be calculated with the weighted mean calculating process, wherein the mean attenuation coefficients $\mu_1(IP3)$, $\mu_2(IP3)$, and $\mu_3(IP3)$ which have been calculated with respect to the third stimulable phosphor sheet IP3 and respectively from the logarithmic radiation dose differences Ia, Ib, and Ic among the stimulable phosphor sheets IP1, IP2, and IP3, are weighted with the coefficients (which maybe represented by $A_{3-1}$, $A_{3-2}$, and $A_{3-3}$) calculated in accordance with the standard deviations of the mean attenuation coefficients $\mu_1(IP3)$, $\mu_2(IP3)$, and $\mu_3(IP3)$. The weighted mean calculating process is made with Formula (45) shown below. In this manner, the mean attenuation coefficient $\mu_{T3}$, which is closest to the true value, is capable of being calculated.

$$\mu_{T2} = \frac{A_{2-1}\mu_1(IP2) + A_{2-2}\mu_2(IP2) + A_{2-3}\mu_3(IP2)}{A_{2-1} + A_{2-2} + A_{2-3}} \quad (44)$$

$$\mu_{T3} = \frac{A_{3-1}\mu_1(IP3) + A_{3-2}\mu_2(IP3) + A_{3-3}\mu_3(IP3)}{A_{3-1} + A_{3-2} + A_{3-3}} \quad (45)$$

In the manner described above, the standard deviation of each of the mean attenuation coefficients $\mu_k(IP1)$, where k=1 to 3, (of each of the bone and the soft tissue) is calculated in accordance with the table T' and the standard deviation of each of the logarithmic radiation dose differences ln(I1)–ln(I2), ln(I1)–ln(I3), and ln(I2)–ln(I3). Also, the standard deviation of each of the mean attenuation coefficients $\mu_k(IP2)$, where k=1 to 3, (of each of the bone and the soft tissue) is calculated in accordance with the table T' and the standard deviation of each of the logarithmic radiation dose differences ln(I1)–ln(I2) ln(I1)–ln(I3), and ln(I2)–ln(I3). Further, the standard deviation of each of the mean attenuation coefficients $\mu_k(IP3)$, where k=1 to 3, (of each of the bone and the soft tissue) is calculated in accordance with the table T' and the standard deviation of each of the logarithmic radiation dose differences ln(I1)–ln(I2), ln(I1)–ln(I3), and ln(I2)–ln(I3). Furthermore, the coefficients $A_{k-1}$, $A_{k-2}$, and $A_{k-3}$, where k=1 to 3, to be utilized in the weighted mean calculating processes are calculated in accordance with the standard deviations of the mean attenuation coefficients $\mu_k(IP1)$, $\mu_k(IP2)$, and $\mu_k(IP3)$, where k=1 to 3. The information representing the coefficients $A_{k-1}$, $A_{k-2}$, and $A_{k-3}$, where k=1 to 3, is stored in the storage means 20. Also, as described above, in the mean attenuation coefficient calculating means 119A, the mean attenuation coefficients $\mu_k(IP1)$ with respect to the first stimulable phosphor sheet IP1, the mean attenuation coefficients $\mu_k(IP2)$ with respect to the second stimulable phosphor sheet IP2, and the mean attenuation coefficients $\mu_k(IP3)$ with respect to the third stimulable phosphor sheet IP3 are calculated. Further, in the weighted mean value calculating means 119B, the mean,value of the mean attenuation coefficients $\mu_k(IP1)$, the mean value of the mean attenuation coefficients $\mu_k(IP2)$, and the mean value of the mean attenuation coefficients $\mu_k(IP3)$ are calculated with the weighted mean calculating processes, wherein the mean attenuation coefficients $\mu_k(IP1)$ the mean attenuation coefficients $\mu_k(IP2)$, and the mean attenuation coefficients $\mu_k(IP3)$ are weighted with the coefficients $A_{k-1}$, $A_{k-2}$, and $A_{k-3}$ having been calculated in accordance with the standard deviations of the mean attenuation coefficients $\mu_k(IP1)$, $\mu_k(IP2)$, and $\mu_k(IP3)$ In this manner, the true mean attenuation coefficients $\mu_T(IP1)$, $\mu_T(IP2)$, and $\mu_T(IP3)$ are capable of being calculated. Specifically, as the true mean attenuation coefficients $\mu_T(IP1)$, $\mu_T(IP2)$, and $\mu_T(IP3)$, the mean attenuation coefficients of the bone and the soft tissue, which are shown below, are calculated.

$\overline{\mu_S}$, $\overline{\mu_S}$ (with respect to the first stimulable phosphor sheet IP1)

$\overline{\mu_S}'$, $\overline{\mu_S}'$ (with respect to the second stimulable phosphor sheet IP2)

$\overline{\mu_S}''$, $\overline{\mu_S}''$ (with respect to the third stimulable phosphor sheet IP3)

In the subtraction processing means 118, the energy subtraction processing is performed on the combination of the image signal S1 and the image signal S2, the combination of the image signal S1 and the image signal S3, or the combination of the image signal S2 and the image signal S3. In cases where the energy subtraction processing is to be performed on the combination of the image signal S1 and the image signal S2, the energy subtraction processing is performed in accordance with Formula (5) and Formula (6) shown above. In cases where the energy subtraction processing is to be performed on the combination of the image signal S1 and the image signal S3, the energy subtraction processing is performed in accordance with Formula (46) and Formula (47) shown below. In cases where the energy subtraction processing is to be performed on the combination of the image signal S2 and the image signal S3, the energy subtraction processing is performed in accordance with Formula (48) and Formula (49) shown below.

$$S_S = \overline{\mu_B}S3 - \overline{\mu_B}''S1 = (\overline{\mu_S\mu_B}'' - \overline{\mu_S}''\overline{\mu_B})t_S + (\overline{\mu_B}I3_0 - \overline{\mu_B}''I1_0) \quad (46)$$

$$S_B = \overline{\mu_S}S3 - \overline{\mu_S}''S1 = (\overline{\mu_S}''\overline{\mu_B} - \overline{\mu_S\mu_B}'')t_B + (\overline{\mu_S}I3_0 - \overline{\mu_S}''I1_0) \quad (47)$$

wherein $\overline{\mu_B}$ represents the mean attenuation coefficient of the bone with respect to the first stimulable phosphor sheet IP1, $\overline{\mu_S}$ represents the mean attenuation coefficient of the soft tissue with respect to the first stimulable phosphor sheet IP1, $\overline{\mu_S}''$ represents the mean attenuation coefficient of the bone with respect to the third stimulable phosphor sheet IP3, $\overline{\mu_S}''$ represents the mean attenuation coefficient of the soft tissue with respect to the third stimulable phosphor sheet IP3, $t_S$ represents the thickness of the bone, $t_B$ represents the thickness of the soft tissue, and each of $I1_0$ and $I3_0$ represents the fixed number depending upon the radiation source.

$$S_S = \overline{\mu_B}'S3 - \overline{\mu_B}''S2 = (\overline{\mu_S}'\overline{\mu_B}'' - \overline{\mu_S}''\overline{\mu_B}')t_S + (\overline{\mu_B}'I3_0 - \overline{\mu_B}''I2_0) \quad (48)$$

$$S_B = \overline{\mu_S}'S3 - \overline{\mu_S}''S2 = (\overline{\mu_S}''\overline{\mu_B}' - \overline{\mu_S}'\overline{\mu_B}'')t_B + (\overline{\mu_S}'I3_0 - \overline{\mu_S}''I2_0) \quad (49)$$

wherein $\overline{\mu_S}'$ represents the mean attenuation coefficient of the bone with respect to the second stimulable phosphor sheet IP2, $\overline{\mu_S}'$ represents the mean attenuation coefficient of the soft tissue with respect to the second stimulable phosphor sheet IP2, $\overline{\mu_S}''$ represents the mean attenuation coefficient of the bone with respect to the third stimulable phosphor sheet IP3, $\overline{\mu_S}''$ represents the mean attenuation coefficient of the soft tissue with respect to the third stimulable phosphor sheet IP3, $t_S$ represents the thickness of the bone, $t_B$ represents the thickness of the soft tissue, and each of $I2_0$ and $I3_0$ represents the fixed number depending upon the radiation source.

The combination of the image signals to be subjected to the energy subtraction processing may be selected previously.

Also, it is not always possible to directly detect the radiation dose with respect to each of the pixel positions on each of the first stimulable phosphor sheet IP1, the second stimulable phosphor sheet IP2, and the third stimulable phosphor sheet IP3. However, when the dose of radiation impinging upon each of the first stimulable phosphor sheet IP1, the second stimulable phosphor sheet IP2, and the third stimulable phosphor sheet IP3 is large, each of the image signal S1, the image signal S2, and the image signal S3, which are obtained respectively from the first stimulable phosphor sheet IP1, the second stimulable phosphor sheet IP2, and the third stimulable phosphor sheet IP3, takes a large signal value. Thus the signal value of the image signal S1 has the correspondence relationship with the radiation dose I1. Also, the signal value of the image signal S2 has the correspondence relationship with the radiation dose I2. Further, the signal value of the image signal S3 has the correspondence relationship with the radiation dose I3. Therefore, in the third embodiment, the image signal S1, the image signal S2, and the image signal S3, which have been obtained from the logarithmic conversion and the analog-to-digital conversion, are utilized respectively as the radiation dose Ii, the radiation dose I2, and the radiation dose I3. In such cases, since the image signal S1, the image signal S2, and the image signal S3 have already been subjected to the logarithmic conversion, the difference signal S1−S2 between the image signal S1 and the image signal S2 corresponds to the logarithmic radiation dose difference ln(I1)−ln(I2). Also, the difference signal S1−S3 between the image signal S1 and the image signal S3 corresponds to the logarithmic radiation dose difference ln(I1)−ln(I3). Further, the difference signal S2−S3 between the image signal S2 and the image signal S3 corresponds to the logarithmic radiation dose difference ln(I2)−ln(I3). Therefore, in the storage means 20, the table T' is stored as the table representing the relationship between the difference signals S1−S2 and the mean attenuation coefficients, the relationship between the difference signals S1−S3 and the mean attenuation coefficients, and the relationship between the difference signals S2−S3 and the mean attenuation coefficients.

Figure 12:
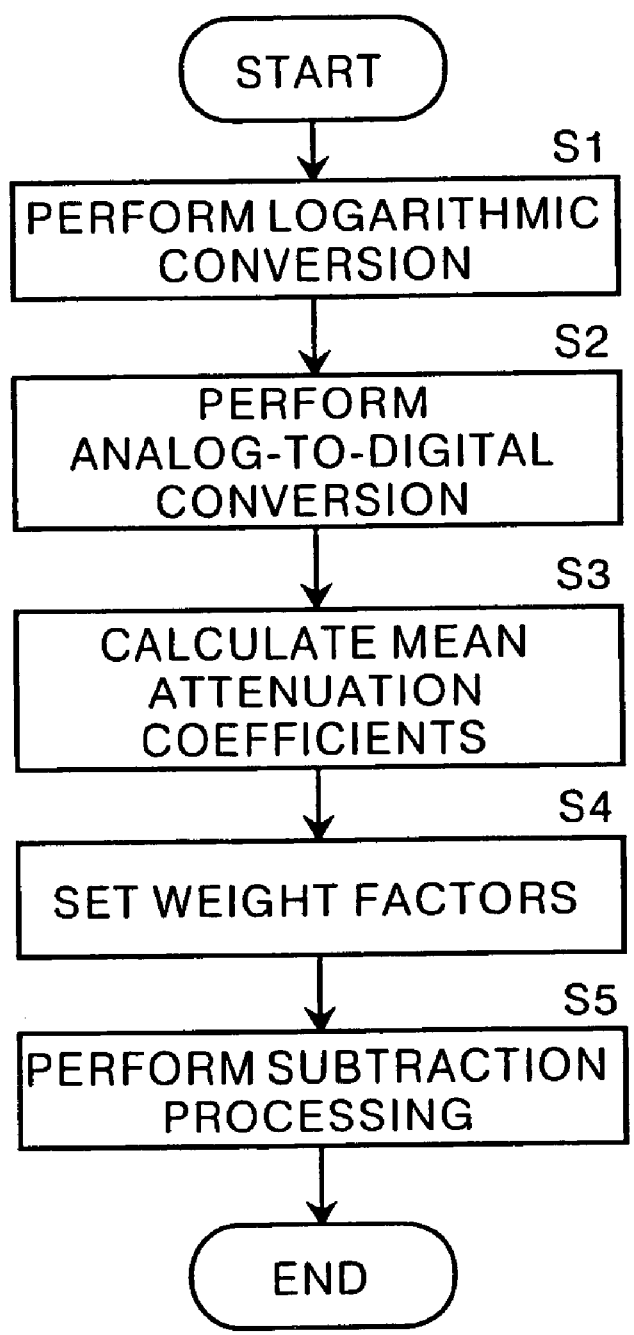
FIG. 12 is a flow chart showing how the third embodiment of the energy subtraction processing apparatus in accordance with the present invention operates.

How the third embodiment of the energy subtraction processing apparatus in accordance with the present invention operates will be described hereinbelow. FIG. 12 is a flow chart showing how the third embodiment of the energy subtraction processing apparatus in accordance with the present invention operates. With reference to FIG. 12, in a step S1, the output signal Q1 having been detected from the first stimulable phosphor sheet IP1, the output signal Q2 having been detected from the second stimulable phosphor sheet IP2, and the output signal Q3 having been detected from the third stimulable phosphor sheet IP3 are subjected to the logarithmic conversion performed by the logarithmic converter 16. In a step S2, the output signal Q1, the output signal Q2, and the output signal Q3, which have been obtained from the logarithmic conversion, are subjected to the analog-to-digital conversion performed by the analog-to-digital converter 17. The digital image signal S1, the digital image signal S2, and the digital image signal S3 are obtained from the analog-to-digital conversion. The digital image signal S1, the digital image signal S2, and the digital image signal S3 are fed into the mean attenuation coefficient calculating means 119A of the setting means 119. In a step S3, in the mean attenuation coefficient calculating means 119A of the setting means 119, the difference signal S1−S2, which corresponds to the logarithmic radiation dose difference ln(I1)−ln(I2), is calculated with respect to the corresponding pixels in the radiation images represented by the image signal S1 and the image signal S2. Also, the difference signal S1−S3, which corresponds to the logarithmic radiation dose difference ln(I1)−ln(I3), is calculated with respect to the corresponding pixels in the radiation images represented by the image signal S1 and the image signal S3. Further, the difference signal S2−S3, which corresponds to the logarithmic radiation dose difference ln(I2)−ln(I3), is calculated with respect to the corresponding pixels in the radiation images represented by the image signal S2 and the image signal S3. Furthermore, reference is made to the table T' in accordance with the difference signals S1−S2, S1−S3, and S2−S3. In this manner, the mean attenuation coefficients of the soft tissue and the bone with respect to the first stimulable phosphor sheet IP1, the mean attenuation coefficients of the soft tissue and the bone with respect to the second stimulable phosphor sheet IP2, and the mean attenuation coefficients of the soft tissue and the bone with respect to the third stimulable phosphor sheet IP3, are calculated. The calculations of the mean attenuation coefficients are made for each of the difference signals S1−S2, S1−S3, and S2−S3.

Also, in a step S4, in the weighted mean value calculating means 119B, with respect to each of the stimulable phosphor sheets IP1, IP2, and IP3, the weighted mean value of the mean attenuation coefficients, which have been calculated respectively for the difference signals S1−S2, S1−S3, and S2−S3, is calculated. The weighted mean values, which have thus been calculated with respect to the stimulable phosphor sheets IP1, IP2, and IP3, are set, as the weight factors. The information representing the weight factors is fed into the subtraction processing means 118. In a step S5, in the subtraction processing means 118, in cases where the energy subtraction processing is to be performed on the image signal S1 and the image signal S2, the energy subtraction processing is performed, wherein the image signal S1 and the image signal S2 are weighted with the weight factors, and the operation processing represented by Formula (5) shown above and the operation processing represented by Formula (6) shown above are performed. From the energy subtraction processing, the difference signal $S_S$ representing the soft tissue image, in which only the pattern of the soft tissue contained in the object 1 is illustrated, and the difference signal $S_B$ representing the bone image, in which only the pattern of the bone contained in the object 1 is illustrated, are obtained. In this stage, the processing with the third embodiment of the energy subtraction processing apparatus in accordance with the present invention is finished. The thus obtained difference signal $S_S$ and the thus obtained difference signal $S_B$ are fed into reproducing means (not shown), such as a printer or a CRT display device, and utilized for reproducing visible images to be utilized in making a diagnosis.

As described above, the third embodiment of the energy subtraction processing apparatus in accordance with the present invention is based on the findings that the certain relationship is obtained between the difference between the logarithmic values of the radiation doses with respect to the two stimulable phosphor sheets among the first stimulable phosphor sheet IP1, the second stimulable phosphor sheet IP2, and the third stimulable phosphor sheet IP3, i.e. the logarithmic radiation dose difference between the two stimulable phosphor sheets, and the mean attenuation coefficient. With the third embodiment, on the basis of the findings described above, the mean attenuation coefficients $\mu_k$(IP1), $\mu_k$(IP2), and $\mu_k$(IP3), where k=1 to 3, are calculated in accordance with the logarithmic radiation dose differences ln(I1)−ln(I2), ln(I1)−ln(I3), and ln(I2)−ln(I3) and for all of the combinations of the two radiation images associated with the calculations of the logarithmic radiation dose differences. Also, the weighted mean value of the mean attenuation coefficients $\mu_k$(IP1) with respect to the first stimulable phosphor sheet IP1, the weighted mean value of the mean attenuation coefficients $\mu_k(IP2)$ with respect to the second stimulable phosphor sheet IP2, and the weighted mean value of the mean attenuation coefficients $\mu_k(IP3)$ with respect to the third stimulable phosphor sheet IP3 are calculated. The weighted mean values, which have thus been calculated, are set as the weight factors to be utilized in the energy subtraction processing.

Therefore, in cases where the energy subtraction processing, in which the weighted mean values having been calculated are utilized as the weight factors for the two image signals among the image signal S1, the image signal S2, and the image signal S3, is performed, the difference signal $S_S$ representing the soft tissue image, in which only the pattern of the soft tissue contained in the object 1 is illustrated accurately, and the difference signal $S_B$ representing the bone image, in which only the pattern of the bone contained in the object 1 is illustrated accurately, are capable of being obtained regardless of the thicknesses of the soft tissue and the bone contained in the object 1.

Also, in the third embodiment described above, the table T', which represents the relationships between the logarithmic radiation dose differences and the mean attenuation coefficients, is determined previously. Therefore, the weight factors are capable of being set easily. Accordingly, the calculation of the difference signal $S_S$ and the calculation of the difference signal $S_B$ are capable of being made efficiently.

Further, as described above, in the strict sense, the mean attenuation coefficient deviates from the true value due to adverse effects of the noise and the scattered radiation. However, with the third embodiment, the plurality of the mean attenuation coefficients $\mu_k(IP1)$ with respect to the first stimulable phosphor sheet IP1, the plurality of the mean attenuation coefficients $\mu_k(IP2)$ with respect to the second stimulable phosphor sheet IP2, and the plurality of the mean attenuation coefficients $\mu_k(IP3)$ with respect to the third stimulable phosphor sheet IP3 are calculated. Also, the weighted mean value of the mean attenuation coefficients $\mu_k(IP1)$, the weighted mean value of the mean attenuation coefficients $\mu_k(IP2)$ and the weighted mean value of the mean attenuation coefficients $\mu_k(IP3)$ are calculated respectively in accordance with the standard deviations of the mean attenuation coefficients $\mu_k(IP1)$ $\mu_k(IP2)$, and $\mu_k(IP3)$. The weighted mean values having thus been calculated are set as the weight factors. Therefore, the mean attenuation coefficients comparatively close to the true values are capable of being utilized in the energy subtraction processing. Accordingly, the pattern of the soft tissue and the pattern of the bone are capable of being extracted accurately.

Figure 13:
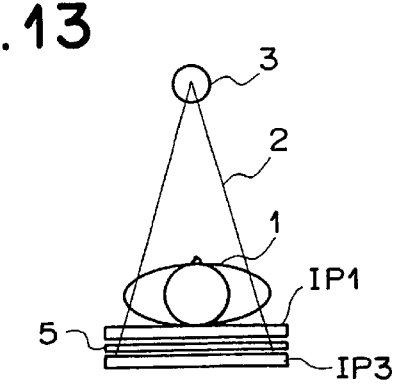
FIG. 13 is a schematic view showing a further different example of how radiation images are recorded on stimulable phosphor sheets.

In the third embodiment described above, the image recording operation is performed on the three stimulable phosphor sheets IP1, IP2, and IP3, and the energy subtraction processing is performed on the two image signals, which are among the image signals S1, S2, and S3 having been obtained from the three stimulable phosphor sheets IP1, IP2, and IP3. Alternatively, as illustrated in FIG. 13, the two stimulable phosphor sheets IP1 and IP3 may be utilized, and the radiation energy converting filter 5 may be located between the two stimulable phosphor sheets IP1 and IP3. In this state, the image recording operation may be performed. Also, the two-surface read-out technique described in, for example, U.S. Pat. No. 4,346,295 may be performed on the stimulable phosphor sheet IP1, and two image signals S1 and 52 maybe obtained from the stimulable phosphor sheet IP1. The two image signals S1 and S2 may be averaged, and a mean image signal Sm may thereby be obtained. Further, the energy subtraction processing may be performed on the mean image signal Sm and the image signal S3, which has been obtained from the stimulable phosphor sheet IP3. A fourth embodiment of the energy subtraction processing apparatus in accordance with the present invention, which is constituted in the manner described above, will be described hereinbelow.

Figure 14:
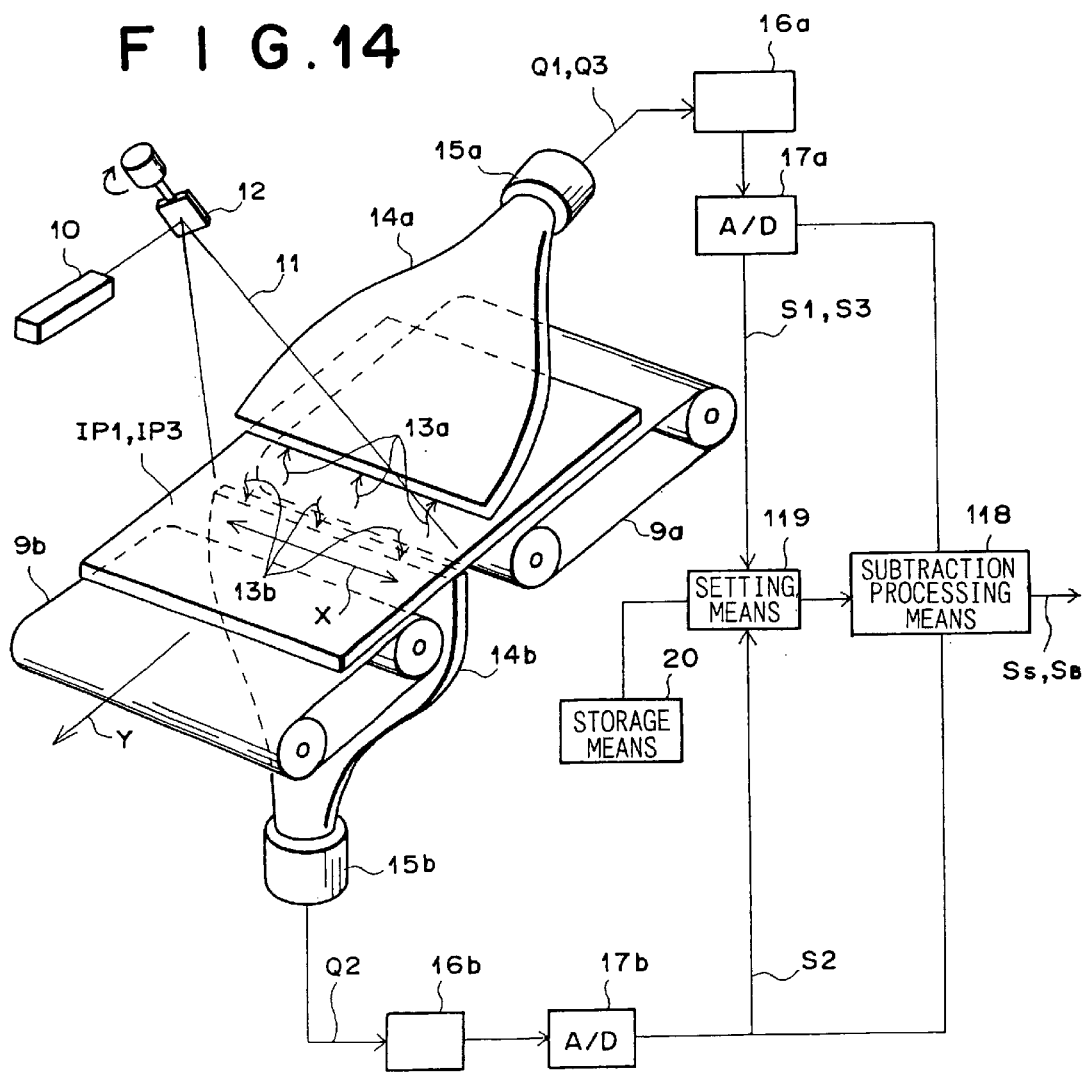
FIG. 14 is a perspective view showing a radiation image read-out apparatus, in which a fourth embodiment of the energy subtraction processing apparatus in accordance with the present invention is employed.

FIG. 14 is a perspective view showing a radiation image read-out apparatus for performing the two-surface read-out technique, in which a fourth embodiment of the energy subtraction processing apparatus in accordance with the present invention is employed. With reference to FIG. 14, the stimulable phosphor sheet IP1 or the stimulable phosphor sheet IP3 is placed on endless belts 9a and 9b and moved in the sub-scanning direction indicated by the arrow Y. The laser beam source 10 and the scanning mirror 12 are located above the endless belts 9a and 9b. The laser beam source 10 produces the laser beam 11 serving as the stimulating rays, which cause the stimulable phosphor sheet IP1 or IP3 to emit light in proportion to the amount of energy stored thereon during its exposure to the radiation. The scanning mirror 12 reflects and deflects the laser beam 11, which has been produced by the laser beam source 10, such that the laser beam 11 may scan the stimulable phosphor sheet IP1 or IP3 in the main scanning directions indicated by the double headed arrow X. A light guide member 14a is located above and close to the position (i.e., the scanning position) on the stimulable phosphor sheet IP1 or IP3, which is being scanned with the laser beam 11. The light guide member 14a collects the light, which is emitted by the stimulable phosphor sheet IP1 or IP3 when it is scanned with the laser beam 11, from above the stimulable phosphor sheet IP1 or IP3. Also, a light guide member 14b is located below the scanning position on the stimulable phosphor sheet IP1 or IP3, which is being scanned with the laser beam 11. The light guide member 14b is located perpendicularly to the stimulable phosphor sheet IP1 or IP3 and collects the light, which is emitted by the stimulable phosphor sheet IP1 or IP3 when it is scanned with the laser beam 11, from below the stimulable phosphor sheet IP1 or IP3. The light guide members 14a and 14b are located such that they may respectively be in close contact with photomultipliers 15a and 15b, which photoelectrically detect the light emitted by the stimulable phosphor sheet IP1 or IP3. The photomultipliers 15a and 15b are respectively connected to logarithmic converters 16a and 16b. The logarithmic converters 16a and 16b are respectively connected to analog-to-digital converters 17a and 17b.

With the radiation image read-out apparatus of FIG. 14, the image read-out operation is performed in the manner described below. Specifically, the stimulable phosphor sheet IP1, on which the radiation image has been stored, is conveyed by the endless belts 9a and 9b in the sub-scanning direction indicated by the arrow Y. Also, the laser beam 11 is produced by the laser beam source 10. The laser beam 11, which has been produced by the laser beam source 10, is reflected and deflected by the scanning mirror 12. The laser beam 11, which has thus been reflected and deflected by the scanning mirror 12, impinges upon the stimulable phosphor sheet IP1 and scans it in the main scanning directions indicated by the double headed arrow X. The main scanning directions are approximately normal to the sub-scanning direction indicated by the arrow Y. When the stimulable phosphor sheet IP1 is exposed to the laser beam 11, the exposed portion of the stimulable phosphor sheet IP1 emits light in proportion to the amount of energy stored thereon during its exposure to the radiation. The light, which is emitted upwardly from the upper surface (the one surface) of the stimulable phosphor sheet IP1, is represented by reference numeral 13a. The light, which is emitted downwardly from the lower surface (the other surface) of the stimulable phosphor sheet IP1, is represented by reference numeral 13b. The emitted light 13a enters into the light guide member 14a from one end face of the light guide member 14a. The emitted light 13a is guided through repeated total reflection inside of the light guide member 14a and detected by the photomultiplier 15a. The photomultiplier 15a generates the analog output signal Q1 corresponding to the intensity of the emitted light 13a, i.e. representing the radiation image having been stored on the stimulable phosphor sheet IP1.

Also, the emitted light 13b enters into the light guide member 14b from one end face of the light guide member 14b. The emitted light 13b is guided through repeated total reflection inside of the light guide member 14b and detected by the photomultiplier 15b. The photomultiplier 15b generates the analog output signal Q2 corresponding to the intensity of the emitted light 13b, i.e. representing the radiation image having been stored on the stimulable phosphor sheet IP1.

The output signal Q1 is logarithmically converted by the logarithmic converter 16a and is then converted by the analog-to-digital converter 17a into the digital image signal S1. Also, the output signal Q2 is logarithmically converted by the logarithmic converter 16b and is then converted by the analog-to-digital converter 17b into the digital image signal S2.

Further, in the same manner as that described above for the stimulable phosphor sheet IP1, the radiation image having been stored on the stimulable phosphor sheet IP3 is read out from the stimulable phosphor sheet IP3. In this case, only the emitted light 13a, which is emitted from the one surface of the stimulable phosphor sheet IP3 when the stimulable phosphor sheet IP3 is scanned with the laser beam 11, is detected by the photomultiplier 15a via the light guide member 14a. In this manner, the output signal Q3 is obtained. The output signal Q3 is logarithmically converted by the logarithmic converter 16a and is then converted by the analog-to-digital converter 17a into the digital image signal S3.

The image signal S1, the image signal S2, and the image signal S3 are fed into the setting means 119. In the setting means 119, in the same manner as that in the third embodiment described above, reference is made to the table T', and the mean attenuation coefficients with respect to the stimulable phosphor sheets IP1 and IP3 are calculated. Also, the weighted mean calculating processes are performed, and the weight factors to be utilized in the energy subtraction processing performed by the subtraction processing means 118 are set.

In the fourth embodiment, the two image signals S1 and S2 are obtained from he stimulable phosphor sheet IP1. Therefore, with respect to the stimulable phosphor sheet IP1, two kinds of the mean attenuation coefficients, i.e. the mean attenuation coefficient with respect to the radiation image detected from the one surface of the stimulable phosphor sheet IP1 and the mean attenuation coefficient with respect to the radiation image detected from the other surface of the stimulable phosphor sheet IP1, are calculated. Specifically, the dose of the radiation impinging upon the one surface of the stimulable phosphor sheet IP1 may be represented by I1, the dose of the radiation impinging upon the other surface of the stimulable phosphor sheet IP1 may be represented by I2, and the dose of the radiation impinging upon the stimulable phosphor sheet IP3 may be represented by I3. Also, the logarithmic radiation dose differences among the radiation doses I1, I2, and I3 may be calculated. Further, it may be regarded that the one surface of the stimulable phosphor sheet IP1 corresponds to the first stimulable phosphor sheet IP1 in the third embodiment described above, and the other surface of the stimulable phosphor sheet IP1 corresponds to the second stimulable phosphor sheet IP2 in the third embodiment described above. In such cases, the mean attenuation coefficients are capable of being calculated in the same manner as that in the third embodiment described above. In the fourth embodiment, the storage means 20 stores the information representing the relationships between each of the logarithmic radiation dose differences and the mean attenuation coefficients with respect to the one surface of the stimulable phosphor sheet IP1, the other surface of the stimulable phosphor sheet IP1, and the stimulable phosphor sheet IP3.

In the manner described above, the mean attenuation coefficients with respect to the one surface of the stimulable phosphor sheet IP1, the other surface of the stimulable phosphor sheet IP1, and the stimulable phosphor sheet IP3 are calculated for each of the logarithmic radiation dose differences. Also, in the same manner as that in the third embodiment described above, the weighted mean value of the mean attenuation coefficients with respect to the one surface of the stimulable phosphor sheet IP1, the weighted mean value of the mean attenuation coefficients with respect to the other surface of the stimulable phosphor sheet IP1, and the weighted mean value of the mean attenuation coefficients with respect to the stimulable phosphor sheet IP3 are calculated. In this manner, for each of the soft tissue and the bone, the true mean attenuation coefficient $\mu_T$ (IP1 one surface) with respect to the one surface of the stimulable phosphor sheet IP1, the true mean attenuation coefficient $\mu_T$ (IP1 other surface) with respect to the other surface of the stimulable phosphor sheet IP1, and the true mean attenuation coefficient $\mu_T$ (IP3) with respect to the stimulable phosphor sheet IP3 are capable of being calculated.

In the fourth embodiment, in the subtraction processing means 118, the mean image signal Sm, which is the mean value of the image signal S1 having been obtained from the one surface of the stimulable phosphor sheet IP1 and the image signal S2 having been obtained from the other surface of the stimulable phosphor sheet IP1, is calculated. Also, the energy subtraction processing is performed on the mean image signal Sm and the image signal S3. Therefore, in the setting means 119, the mean value of the true mean attenuation coefficient $\mu_T$ (IP1 one surface) and the true mean attenuation coefficient $\mu_T$ (IP1 other surface) is calculated as a true mean attenuation coefficient $\mu_{Tm}$ (IP1). The true mean attenuation coefficient $\mu_{Tm}$ (ILL) is utilized as the weight factor for the mean image signal Sm. More specifically, as the true mean attenuation coefficient $\mu_{Tm}$ (IP1), the mean attenuation coefficients of the bone and the soft tissue, which are shown below, are calculated.

$\overline{\mu_{Bm}}, \overline{Sm}$

In the subtraction processing means 118, the energy subtraction processing is performed on the mean image signal Sm and the image signal S3 and in accordance with Formula (50) and $$S_S = \overline{\mu_{Bm}}S3 - \overline{\mu_B}''Sm = (\overline{\mu_{Sm}\mu_B}'' - \overline{\mu_S}''\overline{\mu_{Bm}})t_S + (\overline{\mu_{Bm}}I3_0 - \overline{\mu_B}''Im_0) \quad (50)$$

$$S_B = \overline{\mu_{Sm}}S3 - \overline{\mu_S}''Sm = (\overline{\mu_S}''\overline{\mu_{Bm}} - \overline{\mu_{Sm}\mu_B}'')t_B + (\overline{\mu_{Sm}}I3_0 - \overline{\mu_S}''Im_0) \quad (51)$$

wherein $\overline{\mu_{Bm}}$ represents the mean attenuation coefficient of the bone with respect to the stimulable phosphor sheet IP1, $\overline{\mu_{Sm}}$ represents the mean attenuation coefficient of the soft tissue with respect to the stimulable phosphor sheet IP1, $\overline{\mu_B}''$ represents the mean attenuation coefficient of the bone with respect to the stimulable phosphor sheet IP3, $\overline{\mu_S}''$ represents the mean attenuation coefficient of the soft tissue with respect to the stimulable phosphor sheet IP3, $t_S$ represents the thickness of the bone, $t_B$ represents the thickness of the soft tissue, and each of $Im_0$ and $I3_0$ represents the fixed number depending upon the radiation source.

As described above, in cases where the mean image signal Sm of the image signal S1 and the image signal S2, which have been obtained from the two surfaces of the stimulable phosphor sheet IP1, is calculated, and the energy subtraction processing is performed on the mean image signal Sm and the image signal S3, which has been obtained from the stimulable phosphor sheet IP3, the mean attenuation coefficients are capable of being calculated in the same manner as that in the third embodiment described above. Therefore, regardless of the thicknesses of the soft tissue and the bone contained in the object 1, the difference signal $S_S$ representing the soft tissue image, in which only the pattern of the soft tissue contained in the object 1 is illustrated accurately, and the difference signal $S_B$ representing the bone image, in which only the pattern of the bone contained in the object 1 is illustrated accurately, are capable of being obtained.

In the fourth embodiment, the stimulable phosphor sheet IP1 is scanned with the laser beam 11 having been produced by the one laser beam source 10. Alternatively, the laser beam sources and the scanning mirrors may be located on both the one surface side and the other surface side of the stimulable phosphor sheet IP1, and the laser beams maybe irradiated to the two surfaces of the stimulable phosphor sheet IP1. Also, the light emitted from the one surface of the stimulable phosphor sheet IP1 and the light emitted from the other surface of the stimulable phosphor sheet IP1 may be detected, and the two image signals S1 and S2 may thereby be obtained.

In the third and fourth embodiments described above, the true mean attenuation coefficients are calculated with the weighted mean calculating processes, wherein the mean attenuation coefficients $\mu_k(IP1)$ having been calculated with respect to the first stimulable phosphor sheet IP1, the mean attenuation coefficients $\mu_k(IP2)$ having been calculated with respect to the second stimulable phosphor sheet IP2, and the mean attenuation coefficients $\mu_k(IP3)$ having been calculated with respect to the third stimulable phosphor sheet IP3, where k=1 to 3, are weighted with the coefficients $A_{k-1}$, $A_{k-2}$, and $A_{k-3}$ having been calculated in accordance with the standard deviations of the mean attenuation coefficients $\mu_k(IP1)$, $\mu_k(IP2)$, and $\mu_k(IP3)$. However, the image signal S1, which has been obtained from the first stimulable phosphor sheet IP1 located at the position close to the object 1, contains more of the adverse effects of the scattered radiation than the image signals S2 and S3, which have been obtained from the stimulable phosphor sheets IP2 and IP3 located at the positions remote from the object 1. Therefore, the deviation of the true mean attenuation coefficient $\mu_T(IP1)$, which has been calculated with respect to the first stimulable phosphor sheet IP1, from the true value is large due to the adverse effects of the scattered radiation. Accordingly, for example, as for the first stimulable phosphor sheet IP1, when the true mean attenuation coefficient is calculated with Formula (43) shown above, the coefficients $A_{1-1}$, and $A_{1-2}$ may be multiplied by a coefficient $\alpha(<1)$. In this manner, the weighting of each of the mean attenuation coefficients $\mu_1(IP1)$ and $\mu_2(IP1)$, which have been calculated in accordance with the dose of the radiation impinging upon the first stimulable phosphor sheet IP1, may be set to be light. In such cases, the effects of the mean attenuation coefficients, which deviate largely from the true values due to the scattered radiation, are capable of being suppressed. Therefore, the weight factors are capable of being set more accurately.

Figure 15:
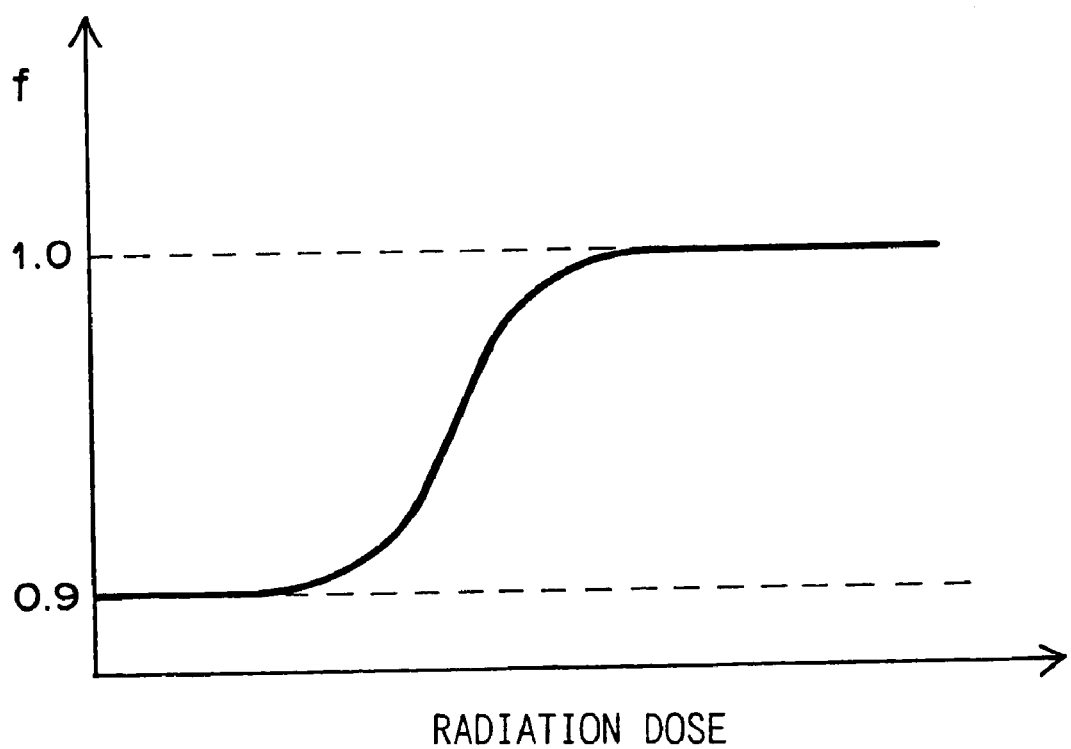
FIG. 15 is a graph showing a function f, whose value becomes small as the radiation dose becomes small.

Further, in cases where the thickness of the object 1 is large, the radiation dose becomes small, and the amount of the scattered radiation becomes large. Therefore, for example, as for the first stimulable phosphor sheet IP1, when the true mean attenuation coefficient is calculated with Formula (43) shown above, the coefficients $A_{1-1}$ and $A_{1-2}$ may be multiplied by a function "f" illustrated in FIG. 15, whose value becomes small when the radiation dose becomes small. In this manner, the weighting of each of the mean attenuation coefficients $\mu_1(IP1)$ and $\mu_2(IP1)$, which have been calculated in accordance with the dose of the radiation impinging upon the first stimulable phosphor sheet IP1, should preferably be set to be light in accordance with the radiation dose, i.e. in accordance with the thickness of the object 1.

In such cases, the adverse effects of the scattered radiation are capable of being minimized. Therefore, the predetermined weight factors are capable of being set more accurately.

In lieu of the weighted mean calculating processes being performed, a simple mean value of the mean attenuation coefficients $\mu_k(IP1)$ having been calculated with respect to the first stimulable phosphor sheet IP1, a simple mean value of the mean attenuation coefficients $\mu_k(IP2)$ having been calculated with respect to the second stimulable phosphor sheet IP2, and a simple mean value of the mean attenuation coefficients $\mu_k(IP3)$ having been calculated with respect to the third stimulable phosphor sheet IP3 may be calculated. The thus calculated simple mean to values maybe employed as the true mean attenuation coefficients.

In the third and fourth embodiments described above, the mean attenuation coefficients are set in accordance with the logarithmic radiation dose difference $\ln(I1)-\ln(I2)$, and so on, among the radiation dose I1, the radiation dose I2, and the radiation dose I3. Alternatively, since the relationship represented by the formula $\ln(I1)-\ln(I2)=\ln(I1/I2)$ is obtained, the mean attenuation coefficients may be set in accordance with the logarithmic value $\ln(I1/I2)$ of the ratio I1/I2 between the radiation dose I1 and the radiation dose I2, the logarithmic value $\ln(I1/I3)$ of the ratio I1/I3 between the radiation dose I1 and the radiation dose I3, and the logarithmic value $\ln(I2/I3)$ of the ratio I2/I3 between the radiation dose I2 and the radiation dose I3.

Also, in the third and fourth embodiments described above, the relationships between the logarithmic radiation dose differences and the mean attenuation coefficients are determined as the table T'. Alternatively, the information representing the functions, which represent the relationships between the logarithmic radiation dose differences and the mean attenuation coefficients, may be stored in the storage means 20, and the mean attenuation coefficient may be calculated from the logarithmic radiation dose differences $\ln(I1)-\ln(I2)$, and so on, by the utilization of each of the functions.

Figure 16:
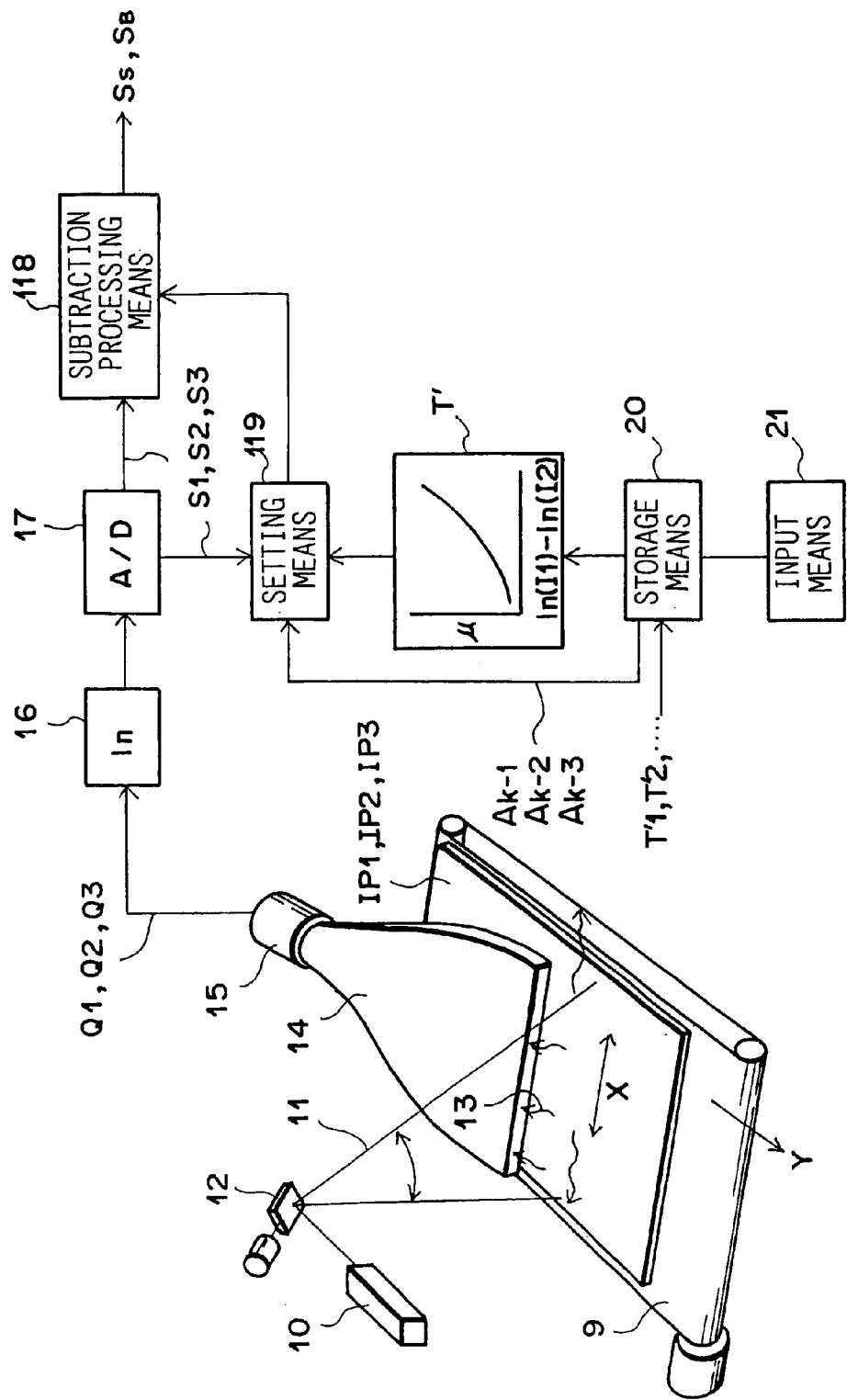
FIG. 16 is a perspective view showing a radiation image read-out apparatus, in which a fifth embodiment of the energy subtraction processing apparatus in accordance with the present invention is employed.

The relationship between the logarithmic radiation dose difference and the mean attenuation coefficient varies for different image recording conditions employed in the image recording operation, such as the voltage of the radiation source 3, the kind of the radiation source 3, and the sensitivities of the first stimulable phosphor sheet IP1, the second stimulable phosphor sheet IP2, and the third stimulable phosphor sheet IP3. Therefore, as in a fifth embodiment of the energy subtraction processing apparatus in accordance with the present invention, which fifth embodiment is illustrated in FIG. 16, a plurality of tables T'1, T'2, . . . in accordance with various different image recording conditions may be prepared previously, and the information representing the plurality of the tables T'1, T'2, . . . may be stored in the storage means 20. Also, the image recording conditions employed in the image recording operation may be inputted from the input means 21, which may be constituted of a keyboard, a mouse device, or the like. Further, a table T' appropriate for the image recording conditions may be selected in accordance with the inputted image recording conditions, and the mean attenuation coefficient may be set by the utilization of the selected table T'.

Further, in the third, fourth, and fifth embodiments described above, the first stimulable phosphor sheet IP1, the second stimulable phosphor sheet IP2, and the third stimulable phosphor sheet IP3 are employed as the radiation detecting means, and the image signal S1, the image signal S2, and the image signal S3 are obtained from the first stimulable phosphor sheet IP1, the second stimulable phosphor sheet IP2, and the third stimulable phosphor sheet IP3. Alternatively, other kinds of radiation detecting means, such as X-ray film and semiconductor sensors, may be employed.

Furthermore, in the third embodiment described above, the one-shot energy subtraction processing technique, wherein the three radiation images to be subjected to the energy subtraction processing are formed simultaneously with one image recording operation, is employed. However, the energy subtraction processing apparatus in accordance with the present invention is not limited to the utilization of the one-shot energy subtraction processing technique. The energy subtraction processing apparatus in accordance with the present invention is also applicable to the cases where a multi-shot energy subtraction processing technique, in which at least three kinds of radiation having different energy distributions are irradiated one after the other to the object, and the radiation images are formed on at least three stimulable phosphor sheets one after the other with at least three image recording operations, is employed, and the image signals obtained with the multi-shot energy subtraction processing technique are subjected to the energy subtraction processing.

In the first, second, third, fourth, and fifth embodiments described above, the object is the human body, and the radiation image representing the soft tissue of the human body and the radiation image representing the bone of the human body are obtained. For example, in industrial product producing fields, radiation images of a certain product are recorded before a durability test is performed and after the durability test has been performed, the energy subtraction processing is performed on image signals representing the radiation images, and a change in structure of the product is thereby detected. Also, in food product producing fields, the energy subtraction processing is performed on an image signal representing a radiation image of a normal food product and an image signal representing a radiation image of a food product to be delivered, and a foreign matter inspection of the food product having been produced is thereby made. The energy subtraction processing apparatus in accordance with the present invention is also applicable to the energy subtraction processing for the fields other than the medical field.

What is claimed is:

1. An energy subtraction processing method, comprising the steps of:

i) obtaining a plurality of image signals, each of which represents one of a plurality of radiation images of a single object and is made up of a series of image signal components, the plurality of the radiation images having been formed respectively with a plurality of kinds of radiation having different energy distributions and carrying image information of the object, different images of at least part of the object being embedded in the plurality of the radiation images, ii) weighting each of the image signals with a predetermined weight factor, and iii) performing a subtraction process on the image signal components of the weighted image signals, which image signal components represent corresponding pixels in the radiation images, a difference signal representing an image of a specific structure of the object being thereby obtained, wherein the improvement comprises the step of:

setting the predetermined weight factor with respect to each of pixels in each of the radiation images and in accordance with a difference between logarithmic values of radiation doses with respect to the corresponding pixels in the radiation images at the time of the formation of the plurality of the radiation images, or in accordance with a logarithmic value of a ratio between the radiation doses with respect to the corresponding pixels in the radiation images at the time of the formation of the plurality of the radiation images.

2. A method as defined in claim 1 wherein reference is made to a table or a function, which represents a relationship between the predetermined weight factor and the difference between the logarithmic values of the radiation doses with respect to the corresponding pixels in the radiation images, or which represents a relationship between the predetermined weight factor and the logarithmic value of the ratio between the radiation doses with respect to the corresponding pixels in the radiation images, the relationship having been determined previously, and the predetermined weight factor is thereby set.

3. A method as defined in claim 2 wherein a plurality of tables or functions, which represent the relationships having been set in accordance with various different image recording conditions at the time of formation of radiation images, are prepared, selection of a table or a function is accepted in accordance with image recording conditions having been set at the time of the formation of the plurality of the radiation images, reference is made to the thus selected table or the thus selected function, and the predetermined weight factor is thereby set.

4. An energy subtraction processing apparatus, comprising:

i) means for obtaining a plurality of image signals, each of which represents one of a plurality of radiation images of a single object and is made up of a series of image signal components, the plurality of the radiation images having been formed respectively with a plurality of kinds of radiation having different energy distributions and carrying image information of the object, different images of at least part of the object being embedded in the plurality of the radiation images, and ii) means for weighting each of the image signals with a predetermined weight factor, and performing a subtraction process on the image signal components of the weighted image signals, which image signal components represent corresponding pixels in the radiation images, in order to obtain a difference signal representing an image of a specific structure of the object, wherein the improvement comprises the provision of:

setting means for setting the predetermined weight factor with respect to each of pixels in each of the radiation images and in accordance with a difference between logarithmic values of radiation doses with respect to the corresponding pixels in the radiation images at the time of the formation of the plurality of the radiation images, or in accordance with a logarithmic value of a ratio between the radiation doses with respect to the corresponding pixels in the radiation images at the time of the formation of the plurality of the radiation images.

5. An apparatus as defined in claim 4 wherein the apparatus further comprises storage means for storing information representing a table or a function, which represents a relationship between the predetermined weight factor and the difference between the logarithmic values of the radiation doses with respect to the corresponding pixels in the radiation images, or which represents a relationship between the predetermined weight factor and the logarithmic value of the ratio between the radiation doses with respect to the corresponding pixels in the radiation images, the relationship having been determined previously, and the setting means makes reference to the table or the function having been stored in the storage means and sets the predetermined weight factor.

6. An apparatus as defined in claim 5 wherein the storage means stores a plurality of tables or functions, which are present the relationships having been set in accordance with various different image recording conditions at the time of formation of radiation images, and the setting means accepts selection of a table or a function in accordance with image recording conditions having been set at the time of the formation of the plurality of the radiation images, makes reference to the thus selected table or the thus selected function, and thereby sets the predetermined weight factor.

7. A recording medium, on which a program for causing a computer to execute an energy subtraction processing method has been recorded and from which the computer is capable of reading the program, the energy subtraction processing method comprising:

i) obtaining a plurality of image signals, each of which represents one of a plurality of radiation images of a single object and is made up of a series of image signal components, the plurality of the radiation images having been formed respectively with; a plurality of kinds of radiation having different energy distributions and carrying image information of the object, different images of at least part of the object being embedded in the plurality of the radiation images, ii) weighting each of the image signals with a predetermined weight factor, and iii) performing a subtraction process on the image signal components of the weighted image signals, which image signal components represent corresponding pixels in the radiation images, a difference signal representing an image of a specific structure of the object being thereby obtained, wherein the program comprises the procedure for:

setting the predetermined weight factor with respect to each of pixels in each of the radiation images and in accordance with a difference between logarithmic values of radiation doses with respect to the corresponding pixels in the radiation images at the time of the formation of the plurality of the radiation images, or in accordance with a logarithmic value of a ration between the radiation doses with respect to the corresponding pixels in the radiation images at the time of the formation of the plurality of the radiation images.

8. A recording medium as defined in claim 7 wherein the procedure for setting the predetermined weight factor is a procedure for:

making reference to a table or a function, which represents a relationship between the predetermined weight factor and the difference between the logarithmic values of the radiation doses with respect to the corresponding pixels in the radiation images, or which represents a relationship between the predetermined weight factor and the logarithmic value of the ratio between the radiation doses with respect to the corresponding pixels in the radiation images, the relationship having been determined previously, and thereby setting the predetermined weight factor.

9. A recording medium as defined in claim 8 wherein, in cases where a plurality of tables or functions, which represent the relationships having been set in accordance with various different image recording conditions at the time of formation of radiation images, are prepared, the procedure for setting the predetermined weight factor is a procedure for:

accepting selection of a table or a function in accordance with image recording conditions having been set at the time of the formation of the plurality of the radiation images, making reference to the thus selected table or the thus selected function, and thereby setting the predetermined weight factor.

10. An energy subtraction processing method, comprising the steps of:

i) obtaining a plurality of image signals, each of which represents one of a plurality of, at least three, radiation images of a single object and is made up of a series of image signal components, the plurality of the radiation images having been formed respectively with a plurality of kinds of radiation having different energy distributions and carrying image information of the object, different images of at least part of the object being embedded in the plurality of the radiation images, ii) weighting each of two representative image signals, which are representative of the plurality of the image signals, with a predetermined weight factor, and iii) performing a subtraction process on the image signal components of the weighted image signals, which image signal components represent corresponding pixels in the two radiation images represented by the two representative image signals, a difference signal representing an image of a specific structure of the object being thereby obtained, wherein the improvement comprises the steps of:

a) setting a mean attenuation coefficient with respect to each of all of the radiation images, with respect to each of pixels in each of the radiation images, and in accordance with a difference between logarithmic values of radiation doses with respect to the corresponding pixels in the radiation images at the time of the formation of the plurality of the radiation images, or in accordance with a logarithmic value of a ratio between the radiation doses with respect to the corresponding pixels in the radiation images at the time of the formation of the plurality of the radiation images, the setting of the mean attenuation coefficient being performed for each of combinations of two radiation images, which two radiation images are associated with a calculation of the difference between the logarithmic values of the radiation doses or a calculation of the logarithmic value of the ratio between the radiation doses and are selected from the plurality of the radiation images, b) calculating a mean value of the mean attenuation coefficients, which have thus been set with respect to an identical radiation image among all of the radiation images and for all of the combinations of the two radiation images selected from the plurality of the radiation images, the mean value of the mean attenuation coefficients being calculated with respect to each of pixels in the identical radiation image, a plurality of mean values being obtained with respect to all of the radiation image, and c) setting representative values of the mean values, which representative values correspond to the radiation images represented by the two representative image signals, as the predetermined weight factors for the two representative image signals.

11. A method as defined in claim 10 wherein reference is made to a table or a function, which represents a relationship between the mean attenuation coefficient and the difference between the logarithmic values of the radiation doses with respect to the corresponding pixels in the radiation images, or which represents a relationship between the mean attenuation coefficient and the logarithmic value of the ratio between the radiation doses with respect to the corresponding pixels in the radiation images, the relationship having been determined previously, and the mean attenuation coefficient is thereby set.

12. A method as defined in claim 11 wherein a plurality of tables or functions, which represent the relationships having been set in accordance with various different image recording conditions at the time of formation of radiation images, are prepared, selection of a table or a function is accepted in accordance with image recording conditions having been set at the time of the formation of the plurality of the radiation images, reference is made to the thus selected table or the thus selected function, and the mean attenuation coefficient is thereby set.

13. A method as defined in claim 10, 11, or 12 wherein the mean value of the mean attenuation coefficients is calculated with a weighted mean calculating process, in which the mean attenuation coefficients are weighted in accordance with standard deviations of the mean attenuation coefficients.

14. A method as defined in claim 13 wherein the weighting of each of the mean attenuation coefficients having been set in accordance with a radiation image, which contains more of scattered radiation than the other radiation images among the plurality of the radiation images, is set to be lighter than the weighting of the mean attenuation coefficient having been set in accordance with the other radiation images.

15. A method as defined in claim 14 wherein, with respect to the radiation image, which contains more of the scattered radiation than the other radiation images, the weighting of each of the mean attenuation coefficients having been set in accordance with the radiation image is set to be light in cases where the radiation dose is small.

16. An energy subtraction processing apparatus, comprising:

i) means for obtaining a plurality of image signals, each of which represents one of a plurality of, at least three, radiation images of a single object and is made up of a series of image signal components, the plurality of the radiation images having been formed respectively with a plurality of kinds of radiation having different energy distributions and carrying image information of the object, different images of at least part of the object being embedded in the plurality of the radiation images, and ii) means for weighting each of two representative image signals, which are representative of the plurality of the image signals, with a predetermined weight factor, and performing a subtraction process on the image signal components of the weighted image signals, which image signal components represent corresponding pixels in the two radiation images represented by the two representative image signals, in order to obtain a difference signal representing an image of a specific structure of the object, wherein the improvement comprises the provision of:

a) mean attenuation coefficient setting means for setting a mean attenuation coefficient with respect to each of all of the radiation images, with respect to each of pixels in each of the radiation images, and in accordance with a difference between logarithmic values of radiation doses with respect to the corresponding pixels in the radiation images at the time of the formation of the plurality of the radiation images, or in accordance with a logarithmic value of a ratio between the radiation doses with respect to the corresponding pixels in the radiation images at the time of the formation of the plurality of the radiation images, the setting of the mean attenuation coefficient being performed for each of combinations of two radiation images, which two radiation images are associated with a calculation of the difference between the logarithmic values of the radiation doses or a calculation of the logarithmic value of the ratio between the radiation doses and are selected from the plurality of the radiation images, b) mean value calculating means for calculating a mean value of the mean attenuation coefficients, which have thus been set with respect to an identical radiation image among all of the radiation images and for all of the combinations of the two radiation images selected from the plurality of the radiation images, the mean value of the mean attenuation coefficients being calculated with respect to each of pixels in the identical radiation image, a plurality of mean values being obtained with respect to all of the radiation image, and c) setting means for setting representative values of the mean values, which representative values correspond to the radiation images represented by the two representative image signals, as the predetermined weight factors for the two representative image signals.

17. An apparatus as defined in claim 16 wherein the apparatus further comprises storage means for storing information representing a table or a function, which represents a relationship between the mean attenuation coefficient and the difference between the logarithmic values of the radiation doses with respect to the corresponding pixels in the radiation images, or which represents a relationship between the mean attenuation coefficient and the logarithmic value of the ratio between the radiation doses with respect to the corresponding pixels in the radiation images, the relationship having been determined previously, and the mean attenuation coefficient setting means makes reference to the table or the function having been stored in the storage means and sets the mean attenuation coefficient.

18. An apparatus as defined in claim 17 wherein the storage means stores a plurality of tables or functions, which represent the relationships having been set in accordance with various different image recording conditions at the time of formation of radiation images, and the mean attenuation coefficient setting means accepts selection of a table or a function in accordance with image recording conditions having been set at the time of the formation of the plurality of the radiation images, makes reference to the thus selected table or the thus selected function, and thereby sets the mean attenuation coefficient.

19. An apparatus as defined in claim 16, 17, or 18 wherein the mean value calculating means is means for calculating the mean value of the mean attenuation coefficients with a weighted mean calculating process, in which the mean attenuation coefficients are weighted in accordance with standard deviations of the mean attenuation coefficients.

20. An apparatus as defined in claim 19 wherein the mean value calculating means sets the weighting of each of the mean attenuation coefficients having been set in accordance with a radiation image, which contains more of scattered radiation than the other radiation images among the plurality of the radiation images, to be lighter than the weighting of the mean attenuation coefficient having been set in accordance with the other radiation images.

21. An apparatus as defined in claim 20 wherein the mean value calculating means operates such that, with respect to the radiation image, which contains more of the scattered radiation than the other radiation images, the weighting of each of the mean attenuation coefficients having been set in accordance with the radiation image is set to be light in cases where the radiation dose is small.

22. A recording medium, on which a program for causing a computer to execute an energy subtraction processing method has been recorded and from which the computer is capable of reading the program, the energy subtraction processing method comprising:

i) obtaining a plurality of image signals, each of which represents one of a plurality of, at least three, radiation images of a single object and is made up of a series of image signal components, the plurality of the radiation images having been formed respectively with a plurality of kinds of radiation having different energy distributions and carrying image information of the object, different images of at least part of the object being embedded in the plurality of the radiation images, ii) weighting each of two representative image signals, which are representative of the plurality of the image signals, with a predetermined weight factor, and iii) performing a subtraction process on the image signal components of the weighted image signals, which image signal components represent corresponding pixels in the two radiation images represented by the two representative image signals, a difference signal representing an image of a specific structure of the object being thereby obtained, wherein the program comprises the procedures for:

a) setting a mean attenuation coefficient with respect to each of all of the radiation images, with respect to each of pixels in each of the radiation images, and in accordance with a difference between logarithmic values of radiation doses with respect to the corresponding pixels in the radiation images at the time of the formation of the plurality of the radiation images, or in accordance with a logarithmic value of a ratio between the radiation doses with respect to the corresponding pixels in the radiation images at the time of the formation of the plurality of the radiation images, the setting of the mean attenuation coefficient being performed for each of combinations of two radiation images, which two radiation images are associated with a calculation of the difference between the logarithmic values of the radiation doses or a calculation of the logarithmic value of the ratio between the radiation doses and are selected from the plurality of the radiation images, b) calculating a mean value of the mean attenuation coefficients, which have thus been set with respect to an identical radiation image among all of the radiation images and for all of the combinations of the two radiation images selected from the plurality of the radiation images, the mean value of the mean attenuation coefficients being calculated with respect to each of pixels in the identical radiation image, a plurality of mean values being obtained with respect to all of the radiation image, and c) setting representative values of the mean values, which representative values correspond to the radiation images represented by the two representative image signals, as the predetermined weight factors for the two representative image signals.

23. A recording medium as defined in claim 22 wherein the procedure for setting the mean attenuation coefficient is a procedure for:

making reference to a table or a function, which represents a relationship between the mean attenuation coefficient and the difference between the logarithmic values of the radiation doses with respect to the corresponding pixels in the radiation images, or which represents a relationship between the mean attenuation coefficient and the logarithmic value of the ratio between the radiation doses with respect to the corresponding pixels in the radiation images, the relationship having been determined previously, and thereby setting the mean attenuation coefficient.

24. A recording medium as defined in claim 23 wherein, in cases where a plurality of tables or functions, which represent the relationships having been set in accordance with various different image recording conditions at the time of formation of radiation images, are prepared, the procedure for setting the mean attenuation coefficient is a procedure for:

accepting selection of a table or a function in accordance with image recording conditions having been set at the time of the formation of the plurality of the radiation images, making reference to the thus selected table or the thus selected function, and thereby setting the mean attenuation coefficient.

25. A recording medium as defined in claim 22, 23, or 24 wherein the procedure for calculating the mean value of the mean attenuation coefficients is a procedure for calculating the mean value of the mean attenuation coefficients with a weighted mean calculating process, in which the mean attenuation coefficients are weighted in accordance with standard deviations of the mean attenuation coefficients.

26. A recording medium as defined in claim 25 wherein the procedure for calculating the mean value of the mean attenuation coefficients is a procedure for:

setting the weighting of each of the mean attenuation coefficients having been set in accordance with a radiation image, which contains more of scattered radiation than the other radiation images among the plurality of the radiation images, to be lighter than the weighting of the mean attenuation coefficient having been set in accordance with the other radiation images, and thereby calculating the mean value of the mean attenuation coefficients.

27. A recording medium as defined in claim 26 wherein the procedure for calculating the mean value of the mean attenuation coefficients is a procedure for operating such that, with respect to the radiation image, which contains more of the scattered radiation than the other radiation images, the weighting of each of the mean attenuation coefficients having been set in accordance with the radiation image is set to be light in cases where the radiation dose is small.

* * * * *